US005760900A

United States Patent [19]
Ito et al.

[11] Patent Number: 5,760,900
[45] Date of Patent: Jun. 2, 1998

[54] METHOD AND APPARATUS FOR OPTICALLY MEASURING SPECIMEN

[75] Inventors: Yuji Ito, Chigasaki; Yoshiyuki Toge; Atsushi Saito, both of Yokohama; Tatsuya Yamazaki, Zushi; Moritoshi Miyamoto, Kawasaki, all of Japan

[73] Assignee: Canon Kabushiki Kaisha, Tokyo, Japan

[21] Appl. No.: 8,993

[22] Filed: Jan. 26, 1993

Related U.S. Application Data

[63] Continuation-in-part of Ser. No. 493,780, Mar. 15, 1990, abandoned, and a continuation-in-part of Ser. No. 921,405, Jul. 31, 1992, abandoned, which is a continuation-in-part of Ser. No. 628,339, Dec. 17, 1990, abandoned.

[30] Foreign Application Priority Data

| Mar. 18, 1989 | [JP] | Japan | 1-067363 |
| Jun. 19, 1989 | [JP] | Japan | 1-156185 |
| Dec. 15, 1989 | [JP] | Japan | 1-325001 |
| Dec. 15, 1989 | [JP] | Japan | 1-325011 |
| Jan. 26, 1990 | [JP] | Japan | 2-016553 |
| Nov. 21, 1990 | [JP] | Japan | 2-318978 |
| Nov. 21, 1990 | [JP] | Japan | 2-318986 |
| Nov. 21, 1990 | [JP] | Japan | 2-318988 |
| Nov. 21, 1990 | [JP] | Japan | 2-318989 |

[51] Int. Cl.$^6$ ............................................. G01N 21/64
[52] U.S. Cl. ............... 356/338; 356/73; 356/339; 356/343; 250/461.2; 435/7.2; 435/808; 436/172
[58] Field of Search ............... 356/335–343, 356/349, 39, 73, 442, 318, 72, 317; 250/573–575, 461.2; 307/427; 435/7.2, 808, 968; 436/528, 531, 533, 537, 548, 172

[56] References Cited

U.S. PATENT DOCUMENTS

| 3,916,197 | 10/1975 | Fulwyler | 356/335 |
| 4,243,318 | 1/1981 | Stohr | 356/39 |
| 4,548,499 | 10/1985 | Eisert et al. | 356/318 |
| 4,573,796 | 3/1986 | Martin et al. | 356/318 |
| 4,599,307 | 7/1986 | Saunders et al. | 435/34 |
| 4,710,635 | 12/1987 | Chupp | 250/461.2 |
| 4,727,020 | 2/1988 | Recktenwald | 435/6 |
| 4,893,929 | 1/1990 | Miyamoto | 356/338 |
| 4,979,818 | 12/1990 | Kobayashi | 356/342 |
| 4,999,513 | 3/1991 | Ito et al. | 356/442 |

OTHER PUBLICATIONS

SteinKamp et al., "Three–color fluorescence measurements on single cells excited at three laser wavelengths," *Cytometry*, vol. 2, No. 4, 1982, pp. 226–231.

*Primary Examiner*—Hoa Q. Pham
*Attorney, Agent, or Firm*—Fitzpatrick, Cella, Harper & Scinto

[57] ABSTRACT

A specimen measurement apparatus and method includes sequentially moving individual specimens, radiating first and second radiation beams on first and second positions spaced apart from each other in a moving direction of the specimens, time-serially detecting light components emerging from specimens passing the first and second positions using the same light detector, and an optical selector, arranged in an optical path between the radiation positions and a light detector, for, when a specimen passes the first position, selectively guiding a light component having a first optical characteristic emerging from the specimen to the light detector, and for, when the specimen passes the second position, selectively guiding a light component having a second optical characteristic emerging from the specimen to the light detector.

30 Claims, 18 Drawing Sheets

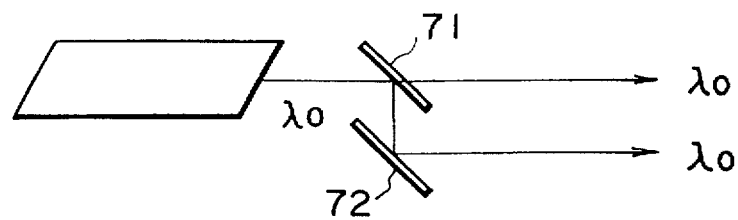
F I G. 11A
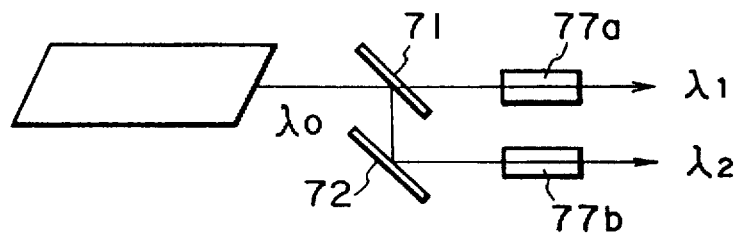
F I G. 11B
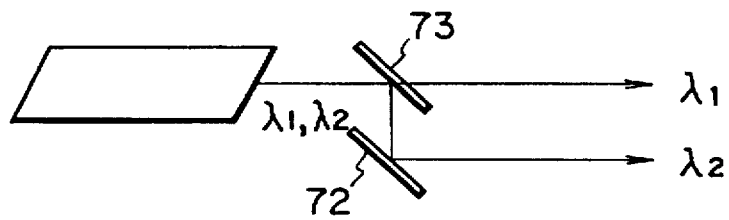
F I G. 11C
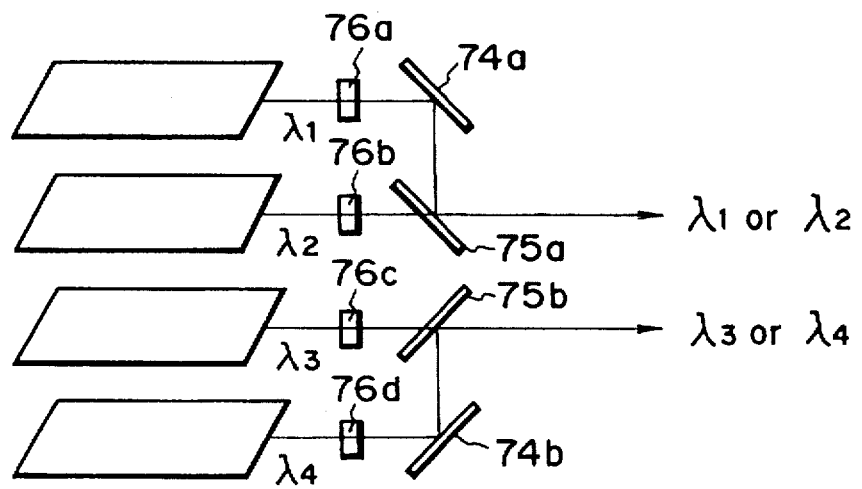
F I G. 11D

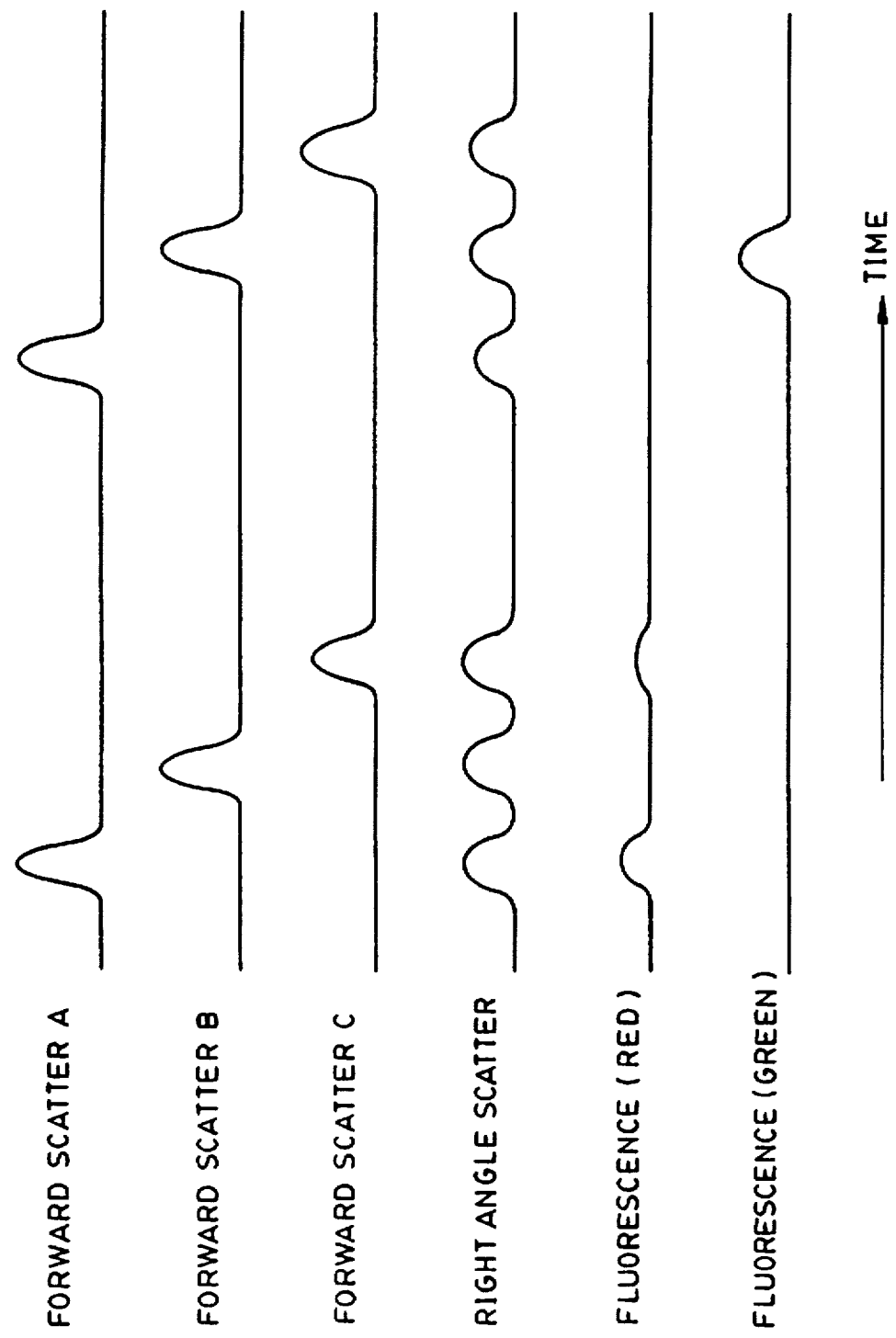

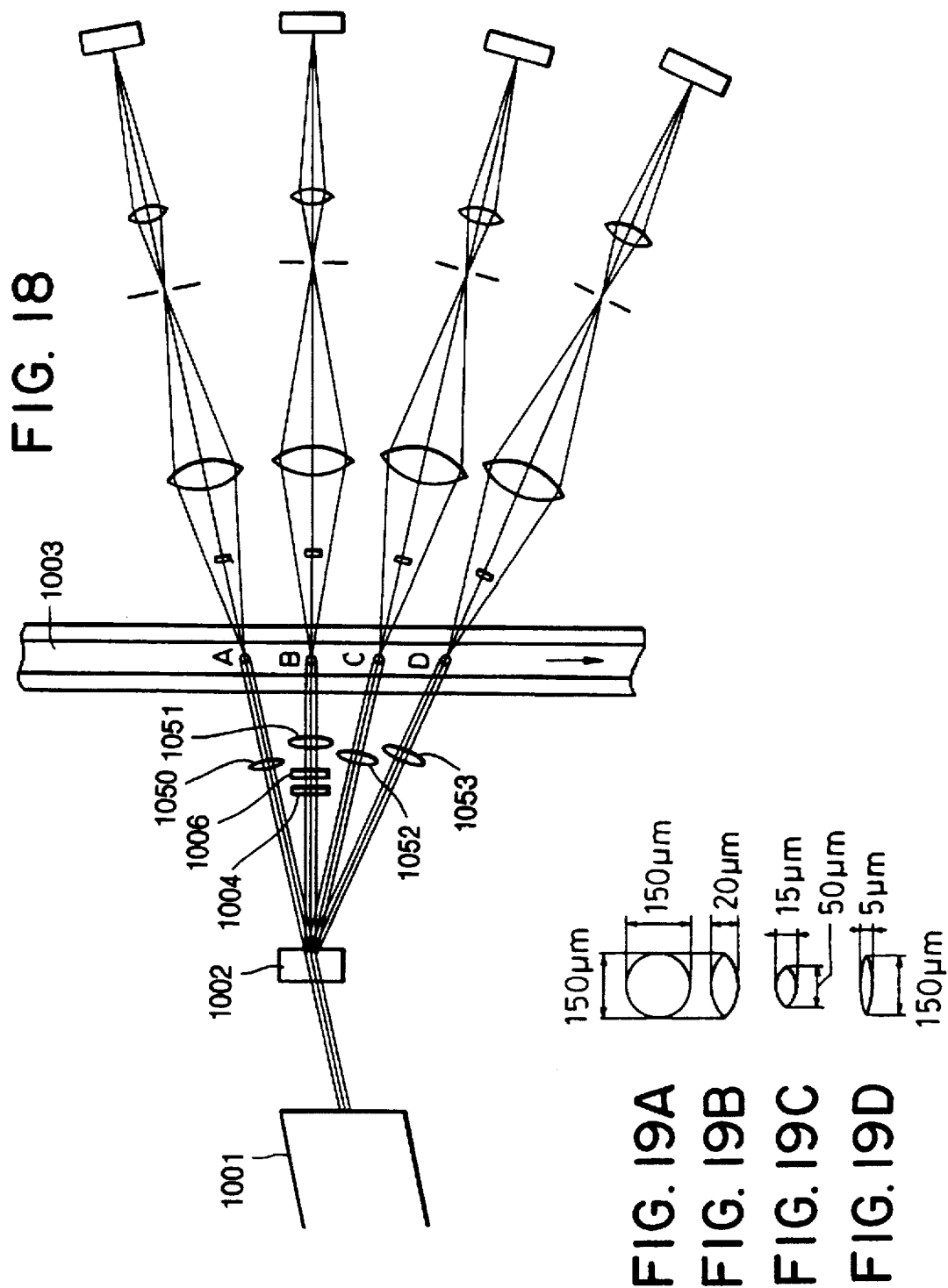

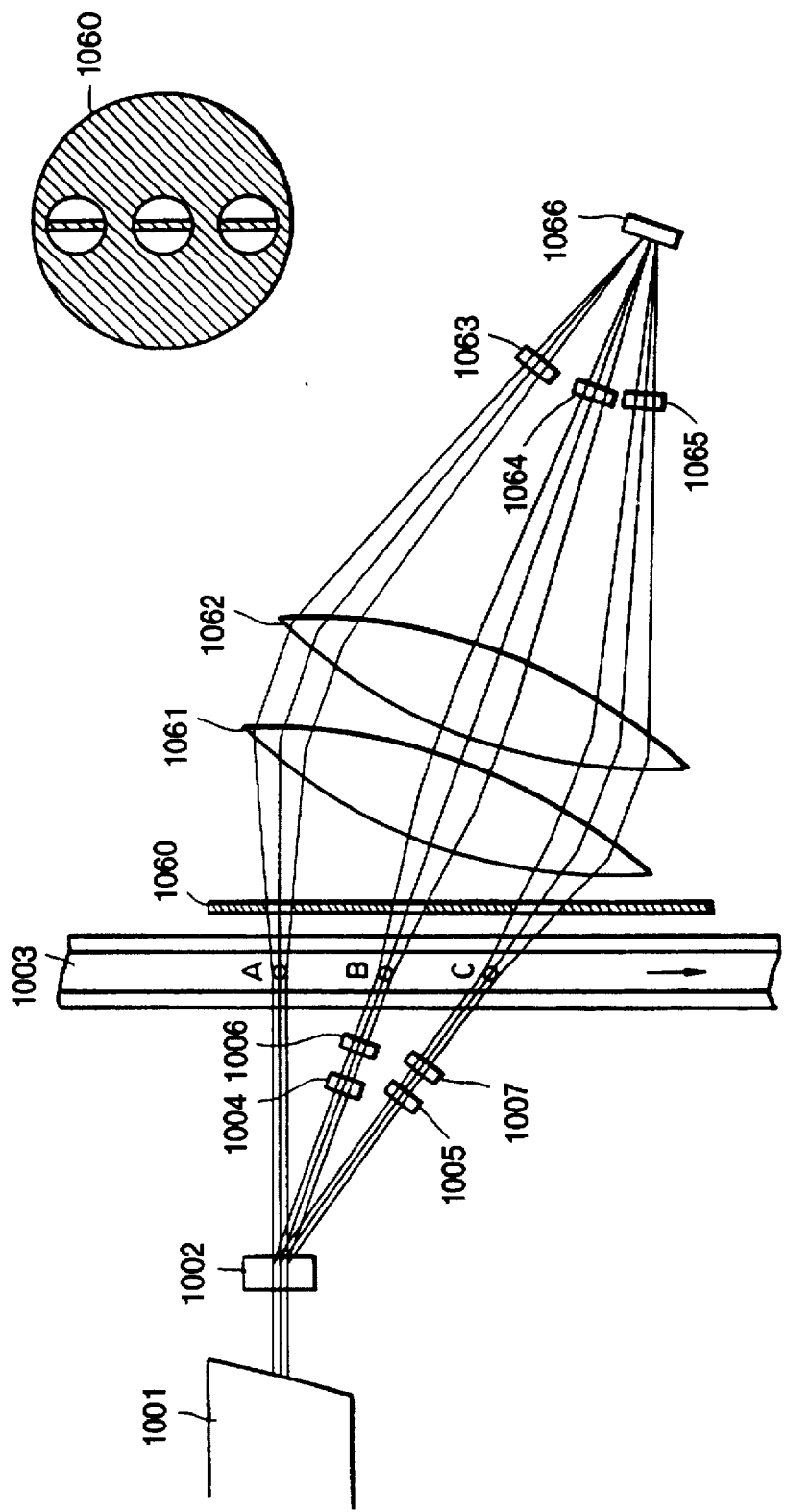

1

METHOD AND APPARATUS FOR OPTICALLY MEASURING SPECIMEN

This application is a continuation-in-part application of pending patent application Ser. No. 493,780 filed Mar. 15, 1990 now abandoned, and pending patent application Ser. No. 921,405 filed Jul. 31, 1992, now abandoned which is a continuation-in-part application of Ser. No. 628,339 filed Dec. 17, 1990, now abandoned.

BACKGROUND OF THE INVENTION

1. Field of the Invention

The present invention relates to a method and apparatus for radiating light on each specimen to perform optical measurement, thereby analyzing the specimen.

2. Related Background Art

As a conventional specimen inspection apparatus, a flow cytometer is known, and is widely used in biological fields and medical fields. The detailed arrangement of the flow cytometer is described in, e.g., U.S. Pat. Nos. 4,243,318, 4,599,307, 4,710,635, 4,727,020, and the like.

FIG. 13 shows a typical arrangement of the flow cytometer. A sample liquid such as blood is dyed with e.g., a fluorescence reagent in a pre-treatment, thereby adjusting it to have proper reaction time and dilution concentration. The sample liquid is put into a sample liquid chamber 115. A sheath liquid such as distilled water or physiologic saline is put into a sample liquid chamber 114. The sample liquid chamber 115 and the sheath liquid chamber 114 are respectively compressed by a compression mechanism (not shown). According to the laminar sheath flow principle, the sample liquid is laminated in the sheath liquid in a flow cell 104, and is converged to a small flow. The small flow passes an almost central portion of a communication portion in the flow cell 104. In this case, individual particles to be examined (cells, microbes, carrier particles, and the like), i.e., specimens are separated, and sequentially flow in units of particles or masses. A laser beam emerging from a laser light source 101 is converged into an arbitrary pattern by a set of cylindrical lenses 102 and 103 the directions of which respectively correspond to a communication portion direction, and a direction perpendicular to the communication portion direction, and the converged beam is radiated on the flow of specimens. The pattern of the light beam radiated onto the specimens is preferably an elliptic pattern having a major axis extending in a direction perpendicular to the flow. This is to radiate a light beam onto the specimens at a uniform intensity even if the position of the flow of specimens varies slightly in the overall flow.

When the light beam is radiated on the specimens, scattered light is generated. Of the scattered light components, a forward scattered light component generated in a forward direction of an optical path is optically detected by a condenser lens 105 and a light detector 106. In order to prevent the radiated light beam from being directly incident on the light detector 106, a small light absorbing stopper 100 is arranged in front of the condenser lens 105 in the optical path, thereby removing direct light from a radiation light source, and transmission light transmitted through the specimens. Thus, only scattered light components from the specimens can be optically detected.

Of the scattered light components, light components generated in a sideward direction perpendicular to a laser optical axis and the flow of specimens are condensed by a condenser lens 107. The condensed light beam is reflected by a dichroic mirror 108, and sideward scattered light is optically detected by a light detector 111 via a band-pass filter 121 for selectively allowing light having a wavelength of scattered light, i.e., a wavelength of the laser beam (488 nm for an AR$^+$ laser) to pass therethrough. If the specimens are dyed with a fluorescence reagent, in order to optically detect a plurality of colors of fluorescence light components generated together with scattered light, of fluorescence light components condensed by the condenser lens 107 and being transmitted through the dichroic mirror 108, a green fluorescence light component is detected by a set of a dichroic mirror 109, a band-pass filter 122 for a green fluorescence light wavelength (near 530 nm), and a light detector 112, and a red fluorescence light component is detected by a set of a total reflection mirror 110, a band-pass filter 123 for a red fluorescence light wavelength (near 570 nm), and a light detector 113. Signals from the light detectors 106, 111, 112, and 113 are inputted to a calculator 116. The calculator 116 performs calculations for analyzing the kind and nature of particles present or measuring an antigen-antibody reaction.

In order to optically detect a plurality of colors of fluorescence light components, however, special-purpose light detectors are used in units of fluorescence light components. To date, an arrangement for simultaneously optically detecting two colors, i.e., red and green fluorescence light components, or three colors including a yellow fluorescence light component in addition to the former two colors has been popular. In recent years, however, demand for an increase in the number of colors has arisen, and new fluorescence agents have been developed. When the number of fluorescence light channels to be used at the same time is increased, the number of light detectors must be increased accordingly. That is, an optical arrangement is complicated, and a large number of expensive light detectors such as photomultipliers are necessary.

U.S. Pat. No. 4,243,318 discloses a system wherein two laser beams having different wavelengths are radiated along a flow direction, and fluorescence light components respectively generated from specimens dyed with two kinds of fluorescence dyes matching with the wavelengths of the two laser beams are detected by a common light-receiving means. However, in this system, since sideward scattered light simultaneously reaches a light detection means together with a target fluorescence light component, it is difficult to precisely detect a target fluorescence light component. Furthermore, when a plurality of colors of fluorescence light components are simultaneously generated, they cannot be separately detected. Therefore, this system cannot be used for measuring two or more colors of fluorescence light components.

U.S. Pat. Nos. 4,599,307, 4,710,635, and 4,727,020 disclose arrangements for commonizing a light detector for receiving time-serially generated forward scattered light components. However, this arrangement does not commonize the light detector commonized in association with fluorescence light or sideward scattered light, and has no arrangement for selecting only a target light component. Thus, light components other than a target light component are undesirably mixed and detected.

By the way, in a conventional apparatus for inspecting particles of a substance to be inspected, for example a flow cytometer, laser light is projected upon a minute particle of the substance to be inspected, the particle being one which is separated individually by a sheath flow method and which flows at high speed, such as a biological cell, a latex particle, a bacterium and the like. Scattered light, fluorescence and the like which are thereby produced are subjected to photometry to obtain information relative to diameters and properties of particles of the substance. The substance is analyzed by statistically processing data thus measured about a large number of particles of the substance.

However, in an ordinary flow cytometer, the irradiating position of a light beam is fixed at one position, and it is therefore impossible to measure the same particle of substance a plurality of times with changing irradiation conditions.

In order to solve this problem, there have been disclosed apparatuses in which two laser light sources are provided and two laser beams are simultaneously projected at different positions in the direction of flow to obtain a plurality of information from the same particle of substance under different irradiation conditions, for example in U.S. Pat. Nos. 3,826,364, 4,599,307, 4,727,020 and the like.

In these apparatuses, however, since laser beams are simultaneously projected at a plurality of adjacent locations, there is the possibility that extrinsic light other than the light from the particle of substance under consideration is mixed in a measured light value, for example if noise components, such as other particles of the substance, dust and the like, simultaneously enter the plural locations.

SUMMARY OF THE INVENTION

It is an object of the present invention to provide a system wherein light components from specimens are time-serially and optically detected so as to obtain measurement parameters in excess of the number of light detectors.

It is another object of the present invention to provide a system which can measure a plurality of colors of fluorescence light components in excess of the number of light detectors.

It is still another object of the present invention to provide a system with high versatility, which can flexibly cope with a large number of different fluorescence dyestuffs.

It is still another object of the present invention to provide a simple system which can measure specimens simultaneously dyed with three or more kinds of fluorescence dyestuffs using a simple arrangement.

It is still another object of the present invention to provide a system which can measure a plurality of light components having different polarization characteristics in excess of the number of light detectors.

It is still another object of the present invention to provide a high-precision system which can precisely detect light components using a single light detector even if time-serially generated light components differ greatly in the amount of light.

It is still another object of the present invention to provide a stable system which can cancel data sampling when a measurement error occurs.

It is still another object of the present invention to provide a system with high versatility, which can switch between a time-serial detection mode and a standard detection mode according to measurement conditions, and can cope with multi-purpose applications.

It is still another object of the present invention to provide an apparatus for inspecting particles capable of switching an irradiating position using deflecting means such as an acousto-optical deflecting device.

It is an object of the present invention to provide an apparatus for inspecting particles which can perform a plurality of measurements for each particle of the substance under the same irradiation condition or under different irradiation conditions in one inspection operation.

It is a further object of the present invention to time serially detect a plurality of information for each particle.

It is a still further object of the present invention to provide an apparatus for inspecting particles capable of performing measurements a plurality of times for each particle with a single light source.

It is still another object of the present invention to provide an apparatus for inspecting particles capable of switching an irradiating position using an acousto-optical deflecting device.

BRIEF DESCRIPTION OF THE DRAWINGS

FIGS. 11A to 12 are diagrams showing modifications of a radiation optical system;

FIG. 17 shows waveforms of output pulses from respective photodetectors;

FIG. 18 is a diagram showing the configuration of a modified example;

FIG. 19 shows the shapes of irradiating spots at portions for inspection in the FIG. 18 embodiment;

FIG. 20 is a diagram showing the configuration of another modified example;

FIG. 21 is a diagram showing the shapes of apertures shown in FIG. 20; and

DETAILED DESCRIPTION OF THE PREFERRED EMBODIMENTS

First Embodiment

An embodiment of the present invention will be described in detail below with reference to the accompanying drawings.

Figure 1:
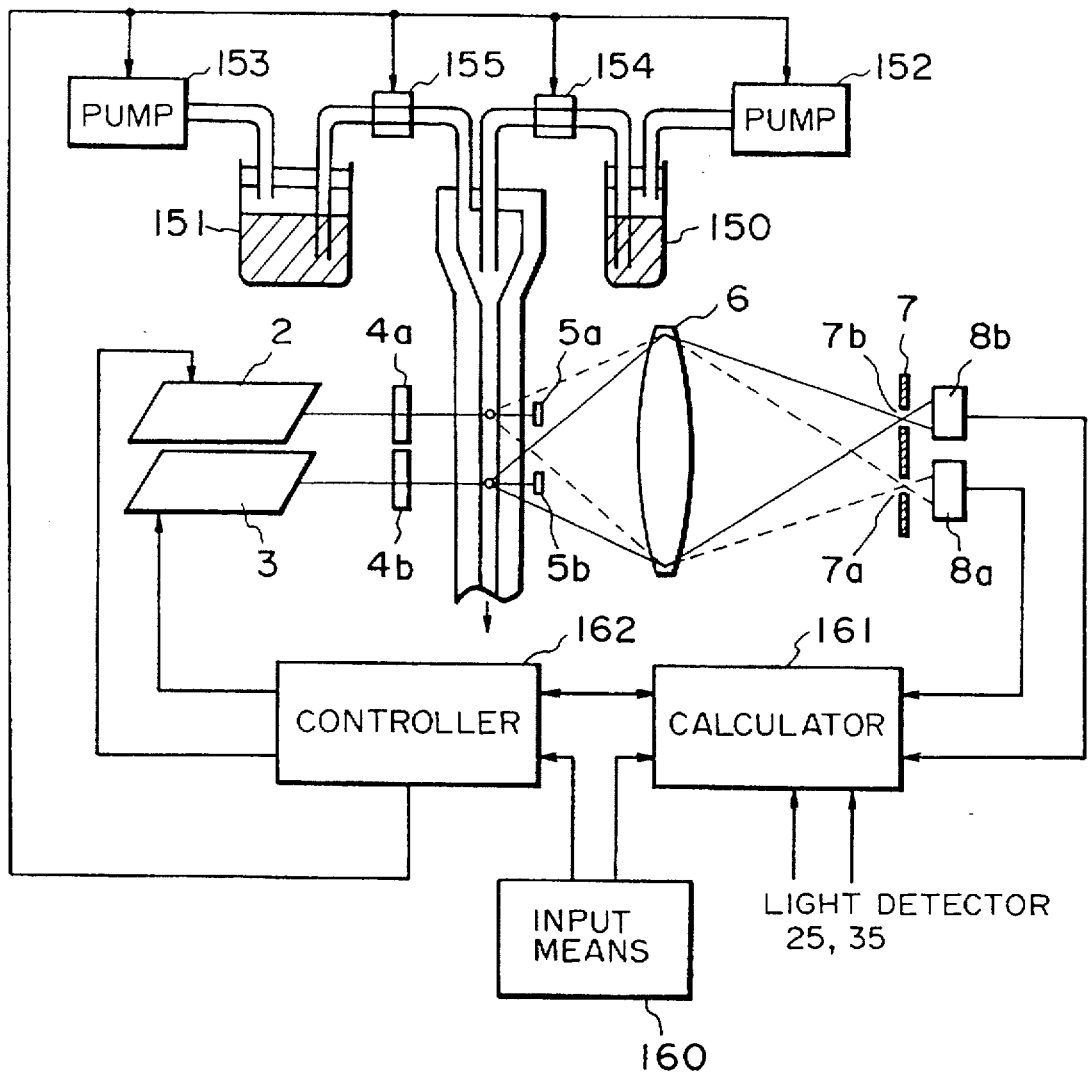
FIGS. 1 and 2 are diagrams showing the first embodiment of the present invention.
Figure 2:
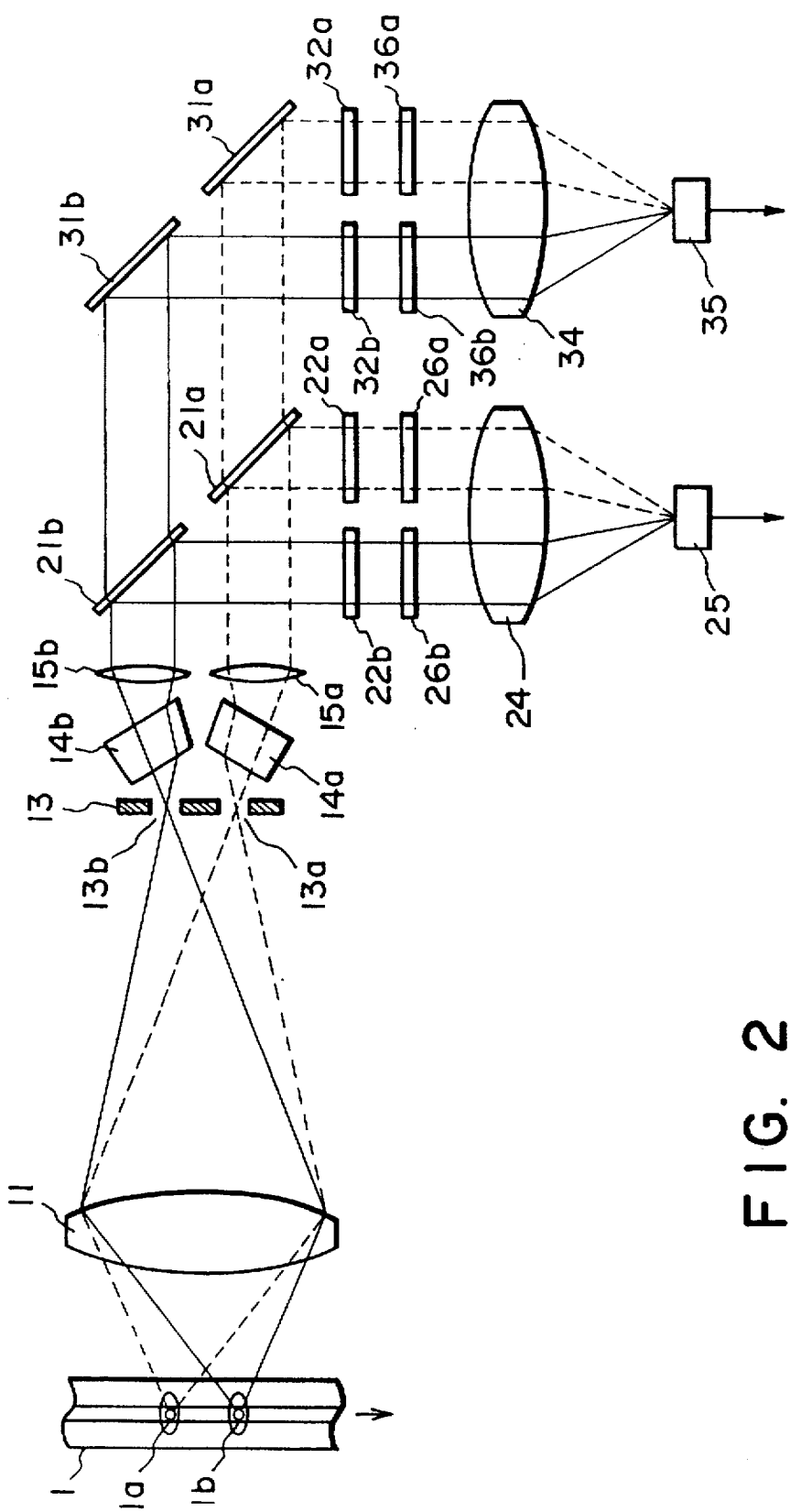

FIGS. 1 and 2 are diagrams showing the first embodiment of the present invention. FIG. 1 shows a basic arrangement of the first embodiment, and illustrates the overall system having a forward optical system, a fluid system, a control system, and the like. In FIG. 1, a flow cell 1 forms a so-called sheath flow for separating particles to be examined (e.g., cells of a living body, carrier particles, and the like; hereinafter referred to as "specimens") in a sample liquid one by one to be laminated in a sheath liquid, and flowing these particles in turn. Particles to be examined flow downward through the drawing surface, i.e., through a communication portion in the flow cell 1. A fluid system for forming the sheath flow comprises a sample liquid chamber 150 for storing a sample liquid such as a blood sample, an immunoreaction liquid, or the like, a pump 152 for compressing the sample liquid, an electrical regulator 154 for regulating a flow rate of the sample liquid, a sheath liquid chamber 151 for storing a sheath liquid such as physiologic saline, a pump 153 for compressing the sheath liquid, an electrical regulator 155 for regulating a flow rate of the sheath liquid, and a tube for connecting these components in a fluid manner, and guiding the liquids into the flow cell 1. The interior of the sample liquid chamber 150 is compressed by the pump 152 to push out the sample liquid. Meanwhile, the interior of the sheath liquid chamber 151 is compressed by the pump 153 to push out the sheath liquid. Then, states in the flow cell 1, i.e., flow velocities, flow intervals of individual particles, and the like, are set under the flow-rate regulation by the regulators 154 and 155. Note that the present invention is not limited to a compression mechanism comprising the pumps and regulators, described above. For example, an arrangement using a syringe disclosed in, e.g., U.S. Ser. No. 476,771 may be employed, so that a push-out velocity of the syringe may be regulated.

A forward optical system will be described below. This system includes laser light sources 2 and 3 having different wavelengths. These laser light sources comprise lasers such as an Ar$^+$ laser, an He—Ne laser, a dye laser, a semiconductor laser, and the like which are popular in this field. Furthermore, the present invention is not limited to a laser, but various other light sources may be utilized. Note that, as shown in FIG. 11D, three or more laser light sources are prepared, and laser beams from these light sources are selectively guided to radiation optical paths in accordance with measurement conditions. Thus, a versatile system which can allow further multi-purpose measurements can be realized. The system shown in FIG. 11D includes a total reflection mirror 74, a half mirror 75, and an optical shutter 76.

Referring back to FIGS. 1 and 2, the forward optical system also includes focusing lenses 4a and 4b for focusing radiation light beams on examination regions of the flow cell portion. These lenses focus laser beams from the laser light sources 2 and 3 at positions 1a and 1b in the flow cell, respectively. Each focused beam spot preferably has an elliptic pattern having a major axis in a direction perpendicular to the flow. A distance between the two radiation positions 1a and 1b is about 100 μm, and is larger than a size of a particle to be measured but is sufficiently smaller than a flow interval of sequentially flowing particles. Light stoppers 5a and 5b are arranged in a beam straight travel direction to shield the laser beams from the laser light sources 2 and 3, thereby forming dark field optical systems. The forward optical system also includes a focusing lens 6 for focusing forward scattered light, a field stop 7 having apertures 7a and 7b at conjugate positions corresponding to positions 1a and 1b, and light detectors 8a and 8b for detecting forward scattered light from positions 1a and 1b.

The two laser light sources need not always be prepared to form two laser beams. For example, as shown in FIGS. 11A, 11B, and 11C, a beam from a single laser light source may be split into two beams by a mirror member. In this case, if an arrangement shown in FIG. 11B or 11C is employed, a plurality of beams having different wavelengths can be obtained. FIG. 11A shows an optical system for splitting a laser beam from a single mode laser having a short wavelength into two laser beams having the same wavelength using the half mirror 71 and the total reflection mirror 72. FIG. 11B shows an optical system for splitting a laser beam into two laser beams using the half mirror 71 and the total reflection mirror 72, and wavelength-modulating these split beams using wavelength conversion members 77a and 77b (e.g., nonlinear optical elements or AO) so as to form two laser beams having different wavelengths. Furthermore, FIG. 11C shows an optical system for splitting a laser beam from a multi-mode laser having a plurality of wavelengths into two laser beams having different wavelengths by using a dichroic mirror 73, thereby forming two laser beams having different wavelengths.

In the arrangement shown in FIG. 1, a laser beam emerging from the laser light source 2 is focused by the focusing lens 4a, and is radiated on the examination region 1a. When specimens pass through the examination region 1a, they cause light scattering. At this time, if the specimens are dyed with fluorescence colors, fluorescence light is also excited, and is generated together with scattered light. Some of the generated scattered light components propagate forward along the optical path, and become forward scattered light components. The forward scattered light components are intensity-detected by the light detector 8a via the focusing lens 6 and the aperture 7a of the field stop 7, thus obtaining a first forward scattered signal. Similarly, a laser beam emerging from the laser light source 3 is focused by the focusing lens 4b, and is radiated on the examination region 1b. When specimens pass through this examination region 1b, forward scattered light components are intensity-detected by the light detector 8b via the aperture 7b, thus obtaining a second forward scattered signal.

A control system of this embodiment includes an input means 160 for inputting and setting various measurement conditions such as various modes of the system, flow velocities and passage intervals of specimens, kinds of fluorescence agent to be used, measurement items, and the like, a calculator 161 for receiving the outputs from the light detectors 8a and 8b, and outputs from light detectors 25 and 23 of a sideward optical system (to be described later) via variable gain amplifiers, peak hold circuits, integration circuits, A/D converters, and the like, and for storing digital data of peak values and integrated values in a memory means. Particle analysis calculations are performed based on the stored data, and calculation results are outputted to an output means such as a CRT, a printer, or the like. As for an analysis method, statistical processing using a histogram or cytogram is popular, and a detailed description thereof will be omitted here. The calculator 161 also has functions of calculating velocities based on two detection output timings of forward scattered light components, canceling sampling of erroneous measurement data, and the like. The control system also includes a controller 162 for systematically controlling various operation means of the system. More specifically, the controller 162 performs drive operations of the pumps 152 and 153, regulation of the electrical regulators 154 and 155, ON/OFF control of the laser light sources 2 and 3, switching of fluorescence detection levels (to be described later), and the like.

A sideward optical system will be described below with reference to FIG. 2. FIG. 2 is a side view of FIG. 1, and illustrates in detail the sideward optical system. The optical system shown in FIG. 2 includes a focusing lens 11 for focusing light components generated in a sideward direction perpendicular to the straight propagation direction of the laser beams radiated from the laser light sources 2 and 3, a field stop 13 having apertures 13a and 13b at conjugate positions corresponding to positions 1a and 1b, parallel plates 14a and 14b, and lenses 15a and 15b. Sets of the parallel plates 14a and 14b and the lenses 15a and 15b convert light components from positions 1a and 1b into parallel light beams. The sideward optical system also includes dichroic mirrors 21a, 21b, 31a, and 31b for color-separating sideward scattered light components and fluorescence light components generated by specimens, and band-pass filters 22a, 22b, 32a, and 32b for selecting wavelengths of corresponding fluorescence light components. Combinations of the dichroic mirrors and the band-pass filters can select corresponding detection light wavelengths. The optical system further includes ND filters 26a, 26b, 36a, and 36b having predetermined transmittances, lenses 24 and 34, and light detectors 25 and 35 for detecting sideward scattered light components and fluorescence light components. As these light detectors, photomultipliers having high detection sensitivity are preferably used. The light detectors 25 and 35 are connected to the calculator 161. Light components emerging from the position 1a are temporarily focused at aperture 13a, are guided to the light detectors 25 and 35 along optical paths consisting of the dichroic mirrors 21a and 31a, the band-pass filters 22a and 32a, and the ND filters 26a and 36a, and are refocused on the detectors 25 and 35. On the other hand, light components emerging from the position 1b are temporarily focused at aperture 13b, are guided toward the light detectors 25 and 35 via optical paths consisting of the dichroic mirrors 21b and 31b, the band-pass filters 22b and 32b, and the ND filters 26b and 36b, and are refocused on the detectors 25 and 35.

Figure 3:
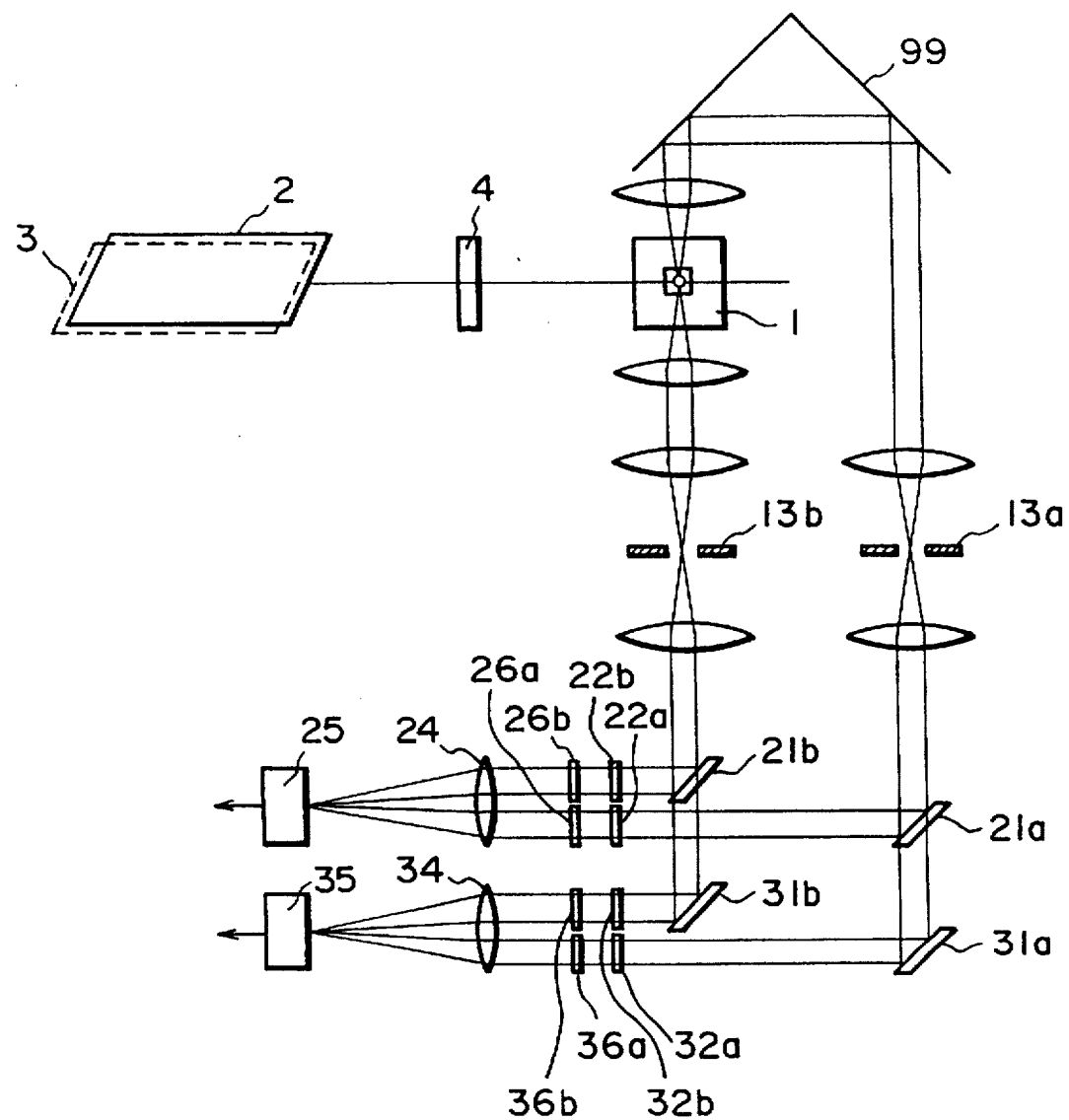
FIG. 3 is a diagram showing a modification of an optical system of the first embodiment.

FIG. 3 shows a modification of the sideward optical system, and is a plan view of FIG. 1. Note that the forward optical system is omitted from FIG. 3. The same reference numerals in FIG. 3 denote the same or equivalent parts as in FIGS. 1 and 2.

Sideward light components emerging from the radiation the position 1a of the laser beam from the laser light source 2 is guided along an optical path in an upper portion of FIG. 3, and is temporarily focused at the aperture stop 13a via a reflection member 99 such as a corner cube or a Porro prism. The focused light components are refocused and incident on the light detectors 25 and 35. On the other hand, sideward light components emerging from the radiation the position 1b of the laser beam from the laser light source 3 are guided along an optical path in a lower portion of FIG. 3, and are temporarily focused at the aperture stop 13b. Thereafter, the focused light components are refocused on and detected by the common light detectors 25 and 35. The arrangement of this modification is basically the same as the optical system shown in FIG. 2. However, the characteristic feature of this modification is that optical paths for detecting fluorescence light components from positions 1a and 1b are distinctly separated and optically arranged.

Figure 4:
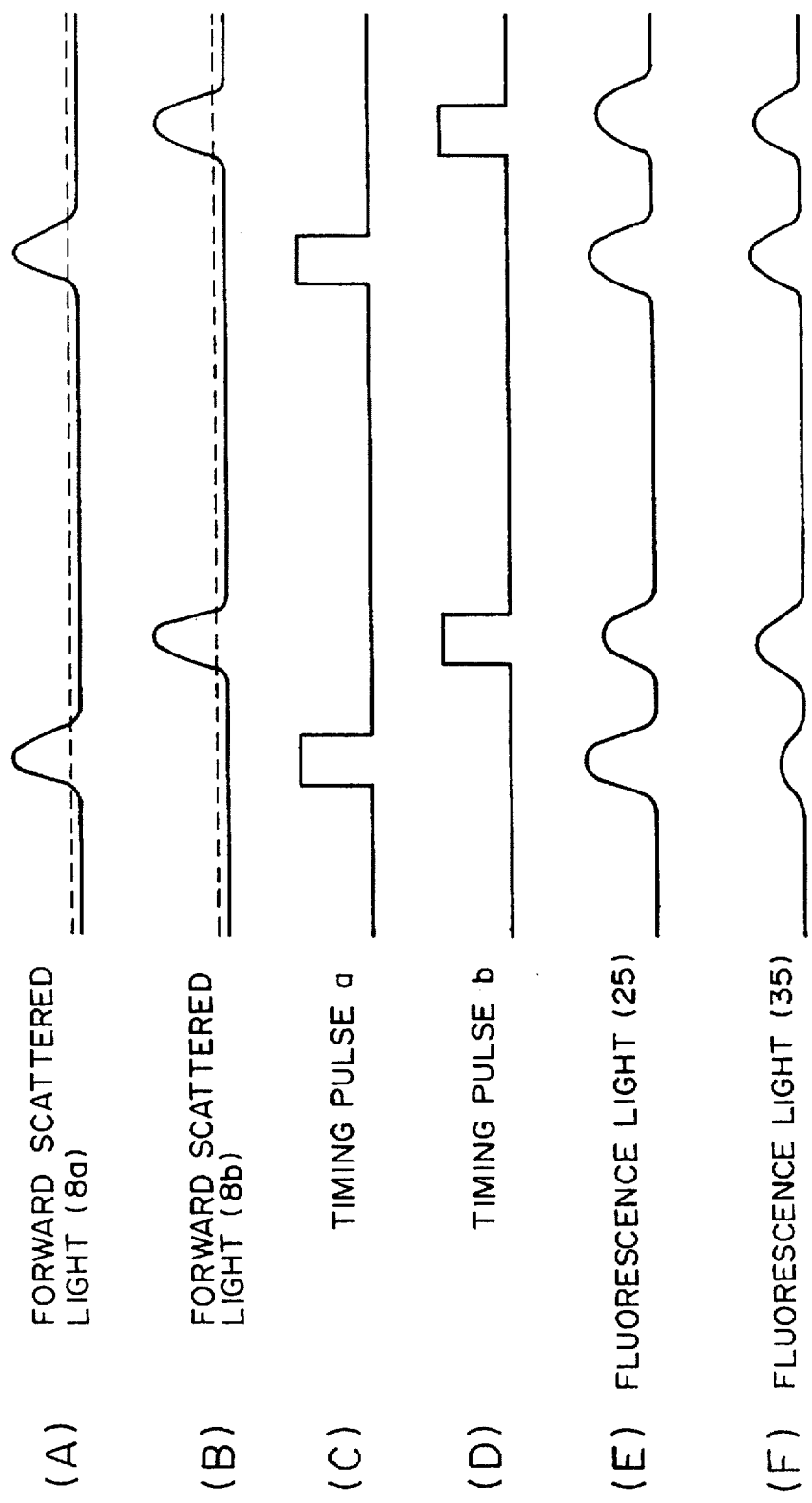
FIGS. 4(A) to 4(F) are signal waveform charts of respective portions of the first embodiment.

FIGS. 4(A) to 4(F) show detection pulses obtained by the respective light detectors. 4(A) and 4(B) respectively show detection outputs of forward scattered light components obtained by the light detectors 8a and 8b, respectively. FIGS. 4(C) and 4(D) show timing pulses generated by comparing the outputs shown in FIGS. 4(A) and 4(B) with a predetermined threshold value, respectively, and FIGS. 4(E) and 4(F) show detection outputs of fluorescence light components obtained by the light detectors 25 and 35, respectively. The detection outputs of fluorescence light components by the light detectors 25 and 35 are time-serially obtained when specimens pass through positions 1a and 1b, and are time-serially collected by utilizing the above-mentioned timing pulses.

As described above, in this embodiment, four-channel detection can be attained by two sideward detectors. Thus, light components of a total of six kinds of different optical characteristics including two forward scattered light components in addition to the above-mentioned channels can be detected.

In the above description, the number of sideward light detectors is two. However, the number of detectors is not limited to this. If a single sideward light detector is arranged, two colors of fluorescence light components can be detected thereby like in the prior art. In this case, the arrangement of the apparatus can be more simplified. If the number of light detectors is three or more, more parameters can be obtained. The sideward light detectors need not always detect fluorescence light components but may detect sideward scattered light components.

The basic arrangement of the system has been described. Characteristic functions of the system of this embodiment will be described below.

(1) Laser Selection According to Measurement Conditions

When the system of this embodiment is put into multi-purpose applications, two laser beam wavelengths need not always be required, and only one wavelength is required depending on measurement objects or kinds of fluorescence agent to be used. Alternatively, when an arrangement as shown in FIG. 11D is employed, i.e., when laser beams from three or more light sources are selectively radiated, an unused laser light wavelength is unnecessary.

The system of this embodiment has a function of switching between a plurality of measurement modes according to applications, and turning off an unused laser beam. More specifically, this system can switch between a first mode for simultaneously radiating two laser beams to perform time-serial measurement, and a second mode for radiating one laser beam and inactivating the other laser light source. The controller 162 independently performs ON/OFF control of the two laser light sources, and sets an unused laser light source in a sleep mode or cuts off a power supply of the laser light source. Thus, low power consumption of the system, and long service life of the lasers can be attained.

(2) Constant Flow Velocity

Since a distance between the two laser radiation positions 1a and 1b is set to be a constant value (about 100 μm), generation timings of the two timing pulses, shown in FIGS. 4(C) and 4(D), generated based on the outputs from the forward scattered light detectors 8a and 8b are compared, and a passage velocity, i.e., a flow velocity of specimens can be obtained based on a time difference between these timings. Comparison between the two timings and calculations of the flow velocity are performed by the calculator 161. The controller 162 always feeds back the flow velocity, thereby adjusting the electrical regulators 154 and 155 to attain the flow velocity set by the input means 160. In this manner, the set velocity can always be precisely maintained, and safety measurement precision can be improved.

Note that the present invention is not limited to a compression mechanism using the pumps and the electrical regulators. For example, a compression mechanism using a syringe may be employed. In this case, a push-out velocity of the syringe is adjusted.

(3) Cancel Sampling of Error Data

A flow interval between sequentially flowing specimens is set to be sufficiently larger than the distance between the two radiation positions 1a and 1b (about 100 µm). However, the specimens do not usually flow within a very small interval, and the two specimens may reach the two positions at substantially the same time. In this case, scattered light components and fluorescence light components are generated from the two positions, and are mixed and incident on the common light detectors. As a result, mixed data are detected.

In order to prevent this, this embodiment comprises a means for detecting whether or not specimens pass positions 1a and 1b at substantially the same time. When it is determined that they pass at substantially the same time, data is cancelled from the detectors to inhibit sampling. More specifically, when the generation timings of the timing pulses shown in FIGS. 4(C) and 4(D) coincide with each other or are very close to each other, the calculator 161 determines that the two specimens pass the two positions 1a and 1b at substantially the same time, and data from the light detectors are canceled to inhibit sampling.

The following method may also be adopted. A time required for moving a specimen from the position 1a to the position 1b can be considered almost constant. Thus, during a predetermined period from when a detection pulse (output from the light detector 8a) is generated when a specimen passes the position 1a until the specimen flows and passes the position 1b, if a detection pulse is generated from the position 1a (output from the light detector 8a), it can be determined that specimens successively flow, and data sampling is canceled.

With the above-mentioned means, since error data can be prevented from being sampled, more reliable measurement can be assured.

(4) Switch Detection Level (1)

In general, fluorescence light and scattered light have considerably different intensity levels, and an amount of fluorescence light greatly varies depending on a kind of fluorescence dyestuff. Therefore, in order to time-serially detect them using the common light detector, a detector having a very wide dynamic range is required. Thus, in this embodiment, passage light amount adjusting means (ND filters 26a, 26b, 36a, and 36b) for adjusting passage light amounts in accordance with an emission amount of fluorescence light to be used are arranged in optical paths extending to the light detectors, so that a difference between amounts of light incident on the light detectors can be minimized. In this manner, an expensive light detector having a wide dynamic range need not be arranged, and a low-cost system can be realized. Note that the present invention is not limited to the ND filters. For example, passage light amounts may be controlled by optical masks for limiting light-shielding areas of optical paths.

If a mechanism capable of exchanging ND filters or a mechanism desirably capable of varying passage light amounts is employed, and is adjusted according to fluorescence dyestuffs to be used, a system having higher versatility can be realized.

(5) Switch Detection Level (2)

In association with switching of the intensity levels, this embodiment also has a circuit for switching gains of the light detectors in accordance with kinds of light to be measured in addition to the ND filters.

More specifically, a circuit for, when the outputs from the light detectors 25 and 35 and input to the calculator 161, switching the gains of the amplifiers in synchronism with passage of specimens at positions 1a and 1b, and a detection sensitivity is switched in accordance with an emission amount of light. The gains are desirably adjusted to cope with various measurement requirements, and the gains of the amplifiers are determined in accordance with measurement conditions input from the input means.

Second Embodiment

The second embodiment will be described below with reference to FIGS. 5 and 6. Note that the same reference numerals in this embodiment denote the same or equivalent parts as in the first embodiment shown in FIGS. 1 and 2, and different portions will be mainly described below.

Figure 5:
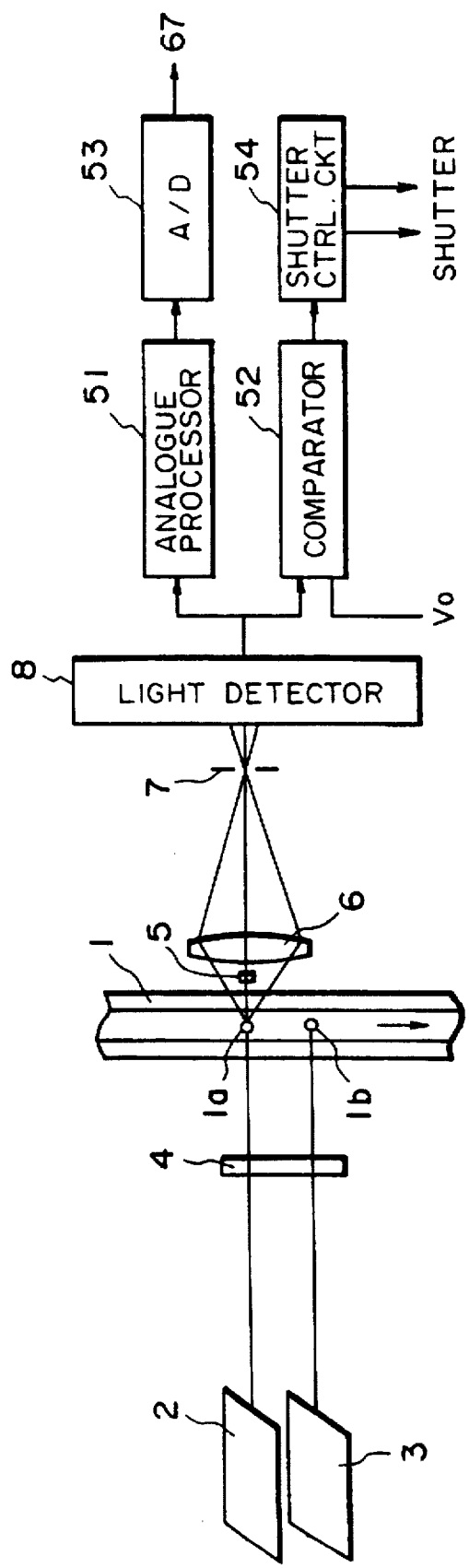
FIGS. 5 and 6 are diagrams showing the second embodiment of the present invention.

FIG. 5 shows in detail a forward optical system. In this embodiment, forward scattered light is detected by a single light detector 8. However, two light detectors may be arranged as in FIG. 1. FIG. 6 is a plan view of the apparatus of this embodiment, and shows in detail a sideward detection optical system. The system shown in FIG. 6 includes shutters 23a, 33a, 43a, 23b, 33b, and 43b capable of shielding light beams. These shutters need only be high-speed shutters which can be independently driven, and various shutters such as mechanical shutters, liquid crystal shutters, AOs, Pockels, cells, or the like may be adopted.

A signal obtained by the light detector 8 is connected to an analogue processor 51 comprising an amplifier, a peak hold circuit, an integration circuit, and the like, and a comparator 52. The output from the analogue processor 51 is connected to an A/D converter 53. Outputs from light detectors 25, 35, and 45 are respectively connected to analogue processors 61, 62, and 63, and A/D converters 64, 65, and 66. The outputs from these A/D converters are supplied to one CPU 67. The CPU 67 is connected to a memory 68. The comparator 52 described above receives a reference voltage $V_0$, and its output is connected to a shutter control circuit 54. Furthermore, the output from the shutter control circuit 54 is connected to the shutters 23a, 23b, 33a, 33b, 43a, and 43b. The shutters are driven as follows. When an application voltage to a shutter is "0", the shutter is opened to allow light to pass therethrough, and when a predetermined voltage $V_1$ is applied to the shutter, the shutter is closed and shields light.

Figure 7:
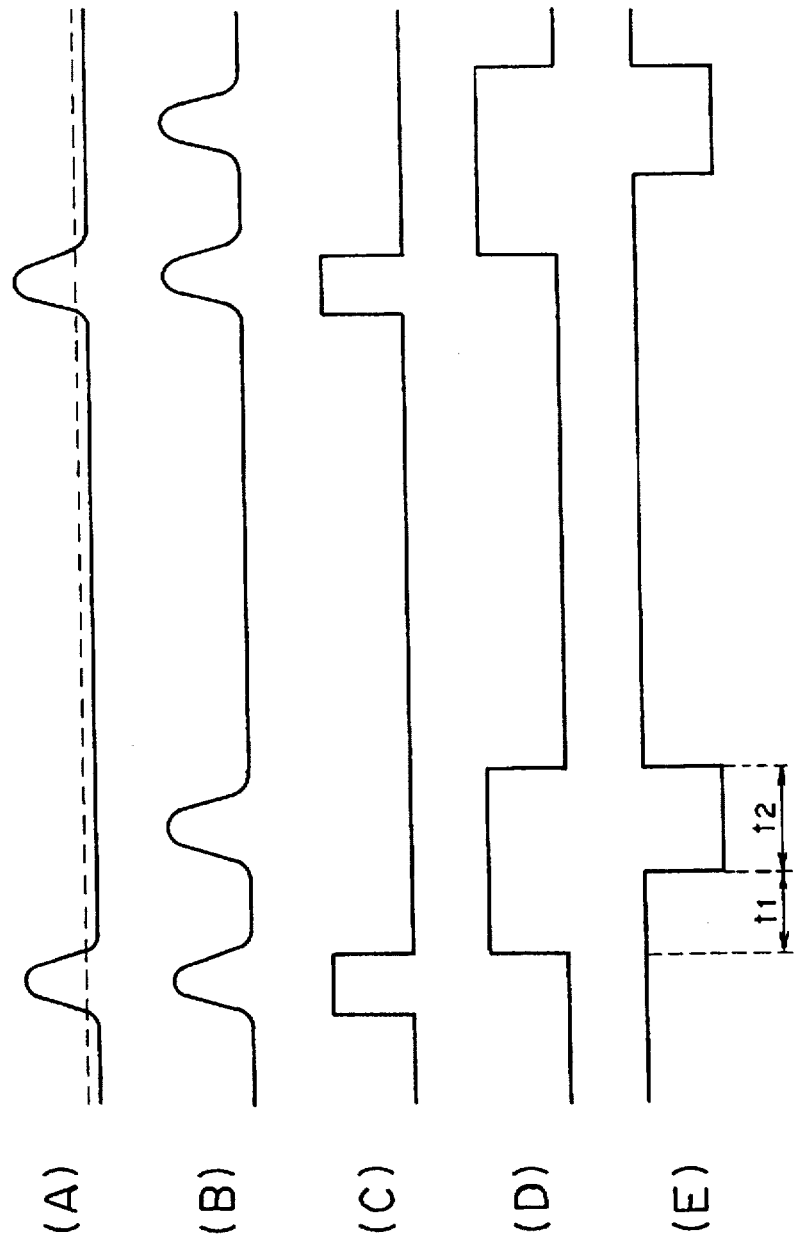
FIGS. 7(A) to 7(E) are signal waveform charts of respective portions of the second embodiment.

An output signal corresponding to a forward scattered light intensity obtained by light detector 8 when a specimen passes the position 1a and crosses a laser beam is as shown in FIG. 7(A). FIG. 7(B) shows an output from the light detector 25, 35, or 45, i.e., an output signal corresponding to a sideward scattered light intensity or a fluorescence light detection intensity. When the output signal from the light detector 8 shown in FIG. 7(A) is compared with the reference voltage $V_0$ as a threshold value by the comparator 52, a timing pulse shown in FIG. 7(C) can be obtained.

Drive signals of the shutters 23a, 33a, and 43a are generated by the shutter control circuit 54 to close the shutters in response to the trailing edge of the timing pulse, as shown in FIG. 7(D), and to open the shutters again in response to the leading edges of the drive signals of the shutters 23b, 33b, and 43b, so that scattered light components and fluorescence light components by a laser beam L1 pass through only the shutters 23a, 33a, and 43a when a specimen passes the position 1a, and scattered light components and fluorescence light components by a laser beam L2 pass through only the shutters 23b, 33b and 43b when a specimen passes the position 1b. The drive signals of the shutters 23b, 33b, and 43b are also generated by the shutter control circuit 54. These drive signals have the following timings, such that the shutters are opened after the lapse of $t_1$ seconds slightly shorter than a time required for a specimen to pass the two lasers from the trailing edge of the timing pulse signal (FIG. 7(C)), i.e., when the specimen reaches a position immediately before the position 1b, and the shutters are closed again after the lapse of $t_2$ seconds corresponding to a time required for the specimen to pass the position 1b, as shown in FIG. 7(E). The above-mentioned control signals perform ON/OFF control of the shutters. When a specimen passes the position 1a, the shutters 23a, 32a, and 33a are opened, and when the identical specimen passes the position 1b, the ON/OFF states of the shutters are reversed.

On the other hand, the outputs from the light detectors 25, 35, and 45 are used to measure peak values obtained when specimens pass the laser light radiation regions, area integration values, and the like in the analogue processors 61, 62 and 63 while switching gains depending on kinds of light to be measured, e.g., fluorescence light. Furthermore, analogue signals from these analogue processors are converted into digital signals by the A/D converters 64, 65, and 66. These digital signals are input to the CPU 67, and are stored in the memory 68. A specimen analysis circuit 69 performs analysis calculations based on measurement data stored in the memory 68, and calculation results are outputted to an output unit 70 such as a CRT, a printer, or the like.

The principle of measurement according to the present invention will be described below.

Normally, the shutters 23a, 33a, and 43a are open, and the shutters 23b, 33b, and 43b are closed. When a specimen passes through the examination region 1a, since an optical path of the shutter 23a is selected, of scattered light components and fluorescence light components generated by the specimen located in the examination region 1a, only a light component which is reflected by the dichroic mirror 21a, and has a specific wavelength (the wavelength of the band-pass filter 22a) via the band-pass filter 22a selectively reaches the light detector 25, and is detected by it. Similarly, scattered light components and fluorescence light components transmitting through the dichroic mirrors 21a and 21b are color-separated by the dichroic mirrors 31a and 31b having different wavelength characteristics, and reflected light components can reach the shutters 33a and 33b. In this case, only a light component reaching the shutter 33a is selected. Thus, only a light component which transmits through the dichroic mirror 21a, is reflected by the dichroic mirror 31a, and has a specific wavelength (the wavelength of the band-pass filter 32a) via the band-pass filter 32a is detected. Furthermore, light components transmitting through the dichroic mirrors 31a and 31b are reflected by the mirrors 41a and 41b, and reach the shutters 43a and 43b via the band-pass filters 42a and 42b having different wavelength characteristics. In this case, only a light component reaching the shutter 43a is selected. Thus, the light detector 45 detects only a light component having a specific wavelength (the wavelength of the band-pass filter 42a), which transmits through the dichroic mirrors 21a and 31a and the band-pass filter 42a.

On the other hand, when the specimen passing through the examination region 1a reaches the examination region 1b after the lapse of a predetermined period of time, the control circuit controls ON/OFF operations of the shutters, so that the shutters 23a, 33a, and 43a are closed, and the shutters 23b, 33b and 43b are open contrary to the above-mentioned case. Thus, optical paths extending from the examination regions to the light detectors are switched. In this manner, light components having specific wavelengths selected by the band-pass filters 22b, 32b, and 42b arranged in the selected optical path are detected by the corresponding detectors.

As described above, ON/OFF operations of the two-divided shutters arranged in front of the light detectors are controlled in synchronism with passage of specimens. In other words, an optical path extending from the examination region to the light detector is divided into two paths, and the optical paths are switched in synchronism with passage of specimens. Thus, a light signal based on the first laser beam and a light signal based on the second laser beam can be time-serially distinguished from each other and can be sampled. As a result, by using the same light detectors and analogue processing system, two kinds of light signal can be measured per detector. More specifically, in the apparatus of this embodiment, which comprises three light detectors in the sideward system, six fluorescent and sideward scattered light components having different parameters can be obtained by these detectors.

As another developed aspect, when the number of divisions of the radiation positions of radiation beams, the dichroic mirrors, the band-pass filters, and shutters is set to be three or more, the number of parameters can be increased. For example, if these components are divided into three sections, three beam radiation positions are set in a flow direction, and the shutters and the like may be equally divided into three sections, as shown in FIG. 5.

The above-mentioned two embodiments exemplify the basic arrangements of the present invention. Some detailed application examples will be described below. Note that kinds and combinations of fluorescence dyestuffs to be used are not limited to those described below, as a matter of course.

APPLICATION EXAMPLE 1

In this example, specimens are simultaneously dyed with three kinds of fluorescence dyestuffs, and are detected in four channels using two light detectors in a sideward optical system.

In FIGS. 1 and 2, the same two $Ar^+$ laser light sources having a wavelength of 488 nm are used as the laser light sources 2 and 3. Note that in place of using two laser light sources, as shown in FIG. 11(A), a laser beam from a single light source may be optically split into two light beams using a half mirror and a total reflection mirror. In this case, it is more preferable to change an intensity ratio of the two laser beams so as to obtain intensities matching with excitation efficiencies of fluorescence agents to be used.

Kinds of fluorescence dyestuffs for dyeing specimens are selected so as to obtain fluorescence light components excited by excitation light having a wavelength of 488 nm. For example, assuming that specimens are dyed with three kinds of fluorescence dyestuffs, e.g., FITC (530 nm), PE (570 nm), and DC (610 nm), light components having four different wavelengths of 488 nm, 530 nm, 570 nm, and 610 nm are simultaneously generated from specimens. Note that the DC cannot be directly excited at the wavelength of 488 nm, but has a stepwise excitation process such that the DC is excited by a fluorescence light component (570 nm) generated when the PE is excited.

After the specimens are dyed with the above-mentioned three kinds of fluorescence dyestuffs in a pre-treatment, they are measured by the apparatus of this embodiment. The light selection wavelengths of the dichroic mirrors 21a, 21b, 31a and 31b are respectively set to be about 510 nm, 590 nm, 450 nm, and 650 nm, and as the band-pass filters 22a, 22b, 32a, and 32b, filters having characteristics for selectively allowing light components having wavelengths near 530 nm, 488 nm, 570 nm, and 610 nm to pass therethrough are used.

Thus, intensity detection operations of FITC, SS (sideward scattered light), PE, and DC are performed by the corresponding optical systems.

When a given specimen passes the position 1a, the four kinds of light components are generated. At this time, the detector 25 detects a fluorescence light intensity of the FITC selected by the band-pass filter 22a, and the detector 35 detects a fluorescence light intensity of the PE selected by the band-pass filter 32a. When the given specimen passes the position 1b the detector 25 detects an SS intensity selected by the band-pass filter 22b, and the detector 35 detects a fluorescence light intensity of the DC selected by the band-pass filter 32b.

In this manner, measurement values of light components having four different optical characteristics can be obtained by the two detectors. A total of six different measurement parameters including two different forward scattered light intensities obtained by the light detectors 8a and 8b in addition to the above-mentioned four parameters can be obtained.

APPLICATION EXAMPLE 2

An application example capable of performing 6-channel detection, i.e., capable of measuring specimens simultaneously dyed with four different fluorescence dyestuffs in the sideward optical system will be described below.

Figure 6:
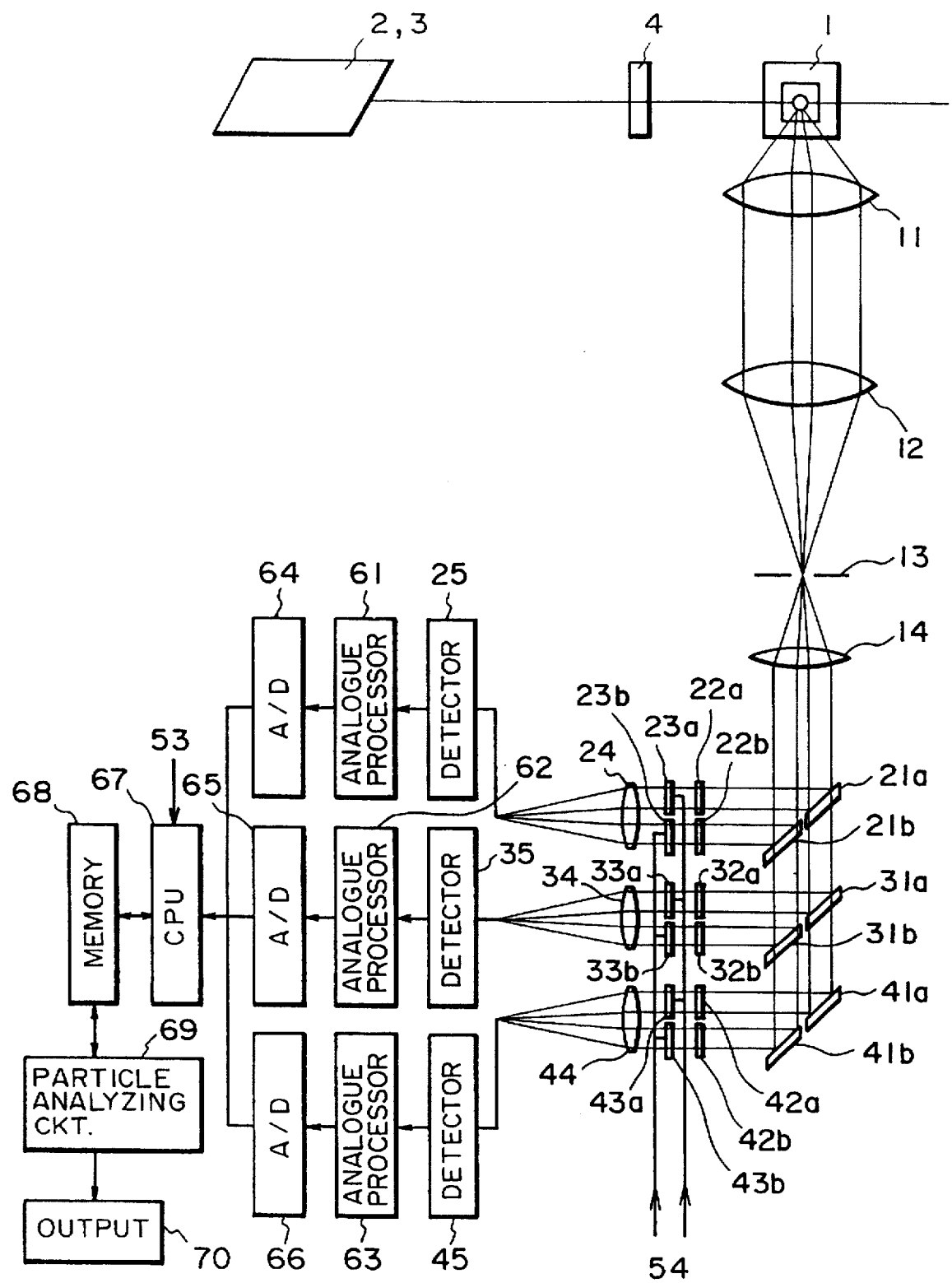

In the optical system shown in FIGS. 5 and 6, or in an optical system having three light detectors obtained by adding another sideward detection system to the arrangement shown in FIG. 2, the laser light source 2 shown in FIG. 2 adopts an $Ar^+$ laser light source having a wavelength of 488 nm, and the laser light source 3 adopts a dye laser light source having a wavelength of 600 nm. Note that if an arrangement shown in FIG. 11B or 11C is adopted, the apparatus can be further simplified.

Fluorescence dyestuffs for dyeing specimens are selected to obtain fluorescence light components excited by excitation light having a wavelength 488 nm, and excited by excitation light having a wavelength of 600 nm. For example, as dyestuffs suitable for 488 nm, FITC (530 nm) and PE (570 nm) are used, and as dyestuffs suitable for 600 nm, TR (610 nm) and APC (660 nm) are used. Thus, specimens are dyed with a total of four different fluorescence dyestuffs.

After the specimens are dyed with the above-mentioned four different fluorescence dyestuffs in a pre-treatment, they are measured by the apparatus of this embodiment. The light selection wavelengths of the dichroic mirrors 21a, 21b, 31a, and 31b are respectively set to be about 570 nm, 605 nm, 550 nm, and 630 nm, and as the band-pass filters 22a, 22b, 32a, 32b, 42a, and 42b, filters having characteristics for selectively allowing light components having wavelengths near 488 nm, 600 nm, 530 nm, 610 nm, 570 nm, and 660 nm to pass therethrough are selected.

When a given specimen passes the position 1a where the $Ar^+$ laser beam is radiated, the FITC and PE are excited by the radiation beam of 488 nm, and three different light components having wavelengths of 488 nm, 530 nm, and 570 nm are generated. At this time, the detector 25 detects SS (488 nm), the detector 35 detects the FITC, and the detector 45 detects the PE. When the given specimen passes the position 1b where the dye laser beam is radiated, the TR and APC are excited by the radiation beam of 600 nm, and three different light components having wavelengths of 600 nm, 610 nm and 660 nm are generated. At this time, the detector 25 detects SS (600 nm), the detector 35 detects the TR, and detector 45 detects the APC.

Where the structure shown in FIGS. 5 and 6 is applied in this example, the shutters are not always required. Since only light components of 488 nm, 530 nm, and 570 nm are generated by the $Ar^+$ laser beam radiated on the position 1a, the respective light detectors can selectively detect the light components of these wavelengths without the shutters. Since only light components of 600 nm, 610 nm and 660 nm are generated by the dye laser beam radiated on the position 1b, the respective light detectors can selectively detect the light components of these wavelengths without the shutters. More specifically, depending on combinations of radiation light wavelengths, kind of fluorescence dyestuffs, and wavelength selection characteristics, the respective parameters can be detected while being distinguished from each other without using the shutters.

In general, radiation beams are selected to have different wavelengths, and characteristics of first and second wavelength selection members such as band-pass filters arranged in front of light detectors are selected such that the first wavelength selection member has characteristics for selecting light having a wavelength, which is generated in response to a first radiation beam but is not generated in response to a second radiation beam, and the second wavelength selection member has characteristics for selecting light having a wavelength, which is generated in response to the second radiation beam but is not generated in response to the first radiation beam. As a result, the shutters can be omitted.

As described above, in this example, detections of a total of six channels, i.e., two channels of sideward scattered light components and four channels of fluorescence light components can be performed by three detectors in the sideward system, and light components of a total of seven different optical characteristics including forward scattered light in addition to the six parameters can be detected.

APPLICATION EXAMPLE 3

Another application example capable of performing 6-channel detection, i.e., capable of measuring specimens simultaneously dyed with four different fluorescence dyestuffs in the sideward optical system as in Application Example 2 described above will be described below.

The laser light source 2 employs an He—Ne laser light source having a wavelength of 633 nm, and the light source 3 employs an $Ar^+$ laser light source having a wavelength of 488 nm. Fluorescence dyestuffs for dyeing specimens, APC (660 nm) and UL (695 nm) are selected as dyestuffs suitable for excitation light of 633 nm, and FITC (530 nm) and PI (620 nm) are selected as dyestuffs suitable for excitation light of 488 nm. Thus, specimens are multiple-dyed with these four different fluorescence dyestuffs.

The light selection wavelengths of the dichroic mirrors 21a, 21b, 31a, and 31b are respectively set to be about 640 nm, 500 nm, 670 nm, and 550 nm, and as the band-pass filters 22a, 22b, 32a, 32b, 42a, and 42b, filters having characteristics for selectively allowing light components have wavelengths near 633 nm, 488 nm, 660 nm, 520 nm, 695 nm, and 620 nm to pass therethrough are selected.

Thus, 6-channel detections can be performed by the sideward optical system having three light detectors as in Application Example 2 described above.

Third Embodiment

The third embodiment of the present invention will be described below with reference to FIG. 8. In place of the shutters in the above embodiments, this embodiment essentially has a shutter function by utilizing the nature of deflection of a laser beam, thus obtaining the same effects as described above. Since this embodiment has an arrangement similar to those in the above embodiments, different portions will be mainly described below. The same reference numerals in this embodiment denote the same or equivalent parts as in the above embodiments.

Figure 8:
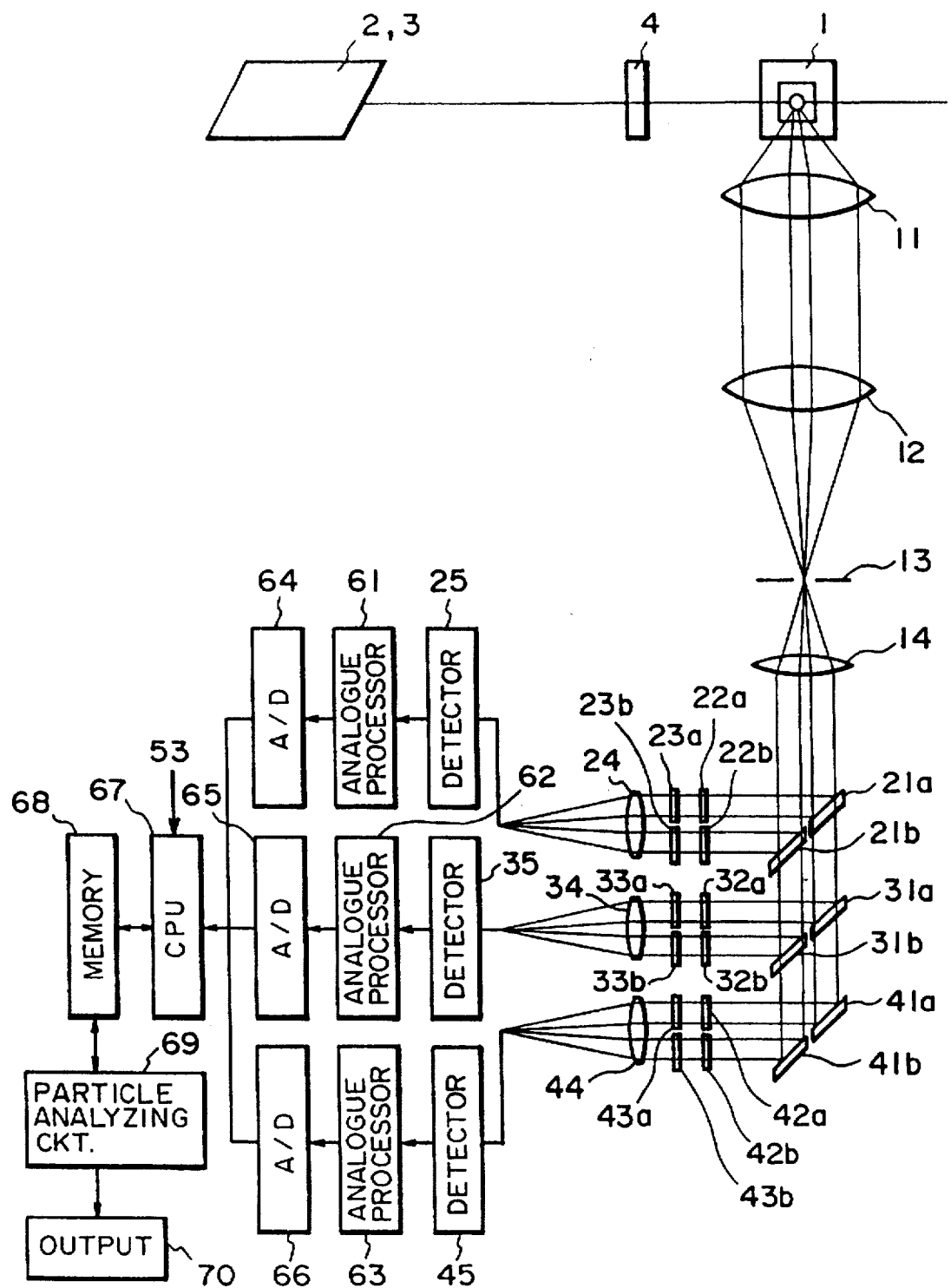
FIG. 8 is a diagram showing the third embodiment of the present invention.
Figure 12:
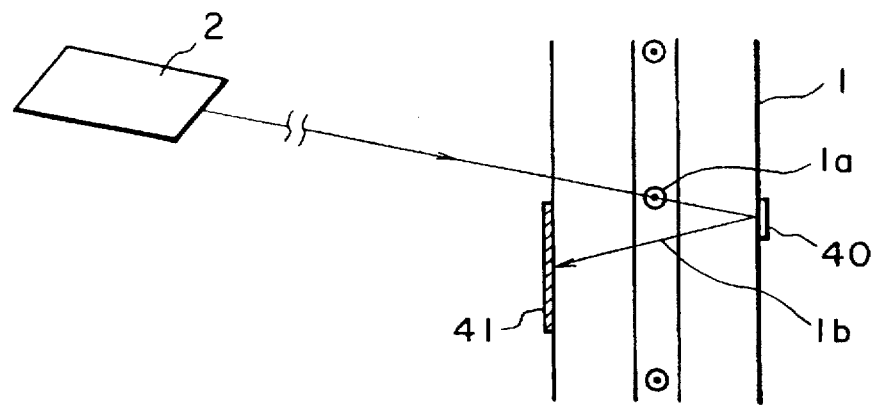
Figure 13:
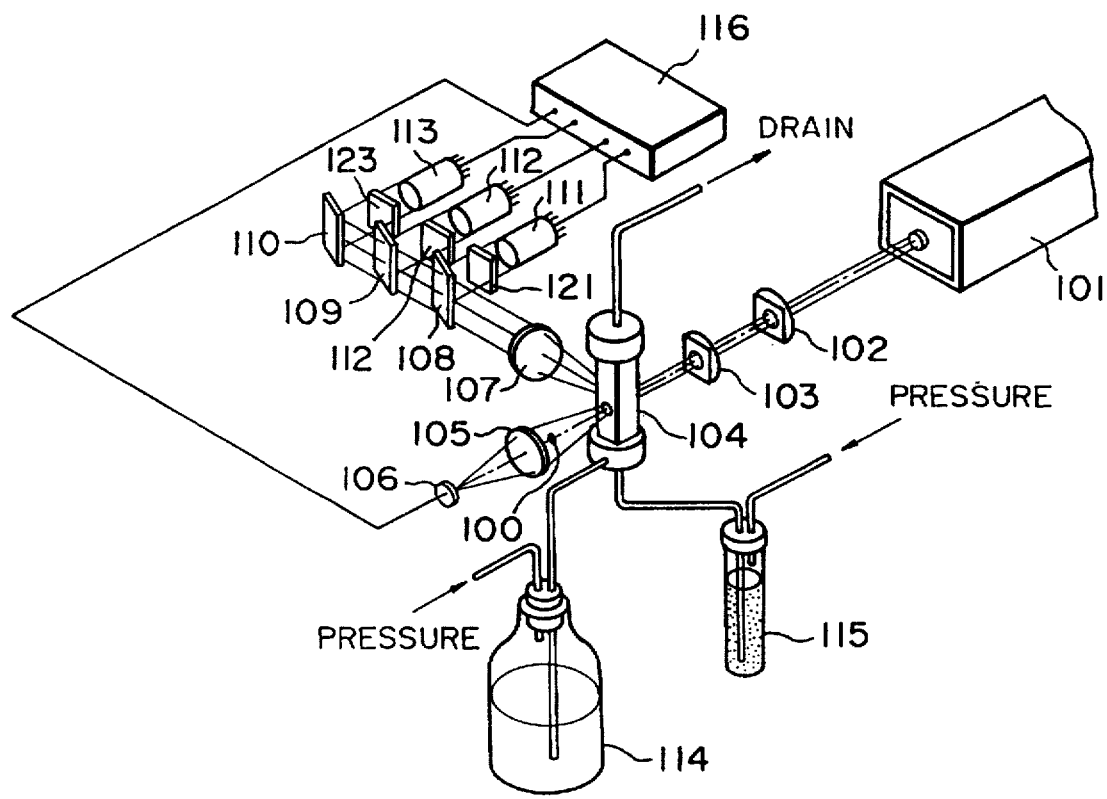
FIG. 13 is a diagram showing a conventional arrangement.

Laser light sources 2 and 3 comprise linearly polarized laser light sources (Ar⁺ lasers in this embodiment), and are arranged so that directions of polarization of the two laser beams are perpendicular to each other, as indicated by an arrow in FIG. 8. This arrangement can be attained by rotating the arrangement direction of one laser light source through 90° or by arranging a λ/2 plate in an optical path of one laser light source. FIG. 12 shows a modification which can obtain the same effect as in the above arrangement by a simpler arrangement. A linearly polarized laser beam emerging from the laser light source 2 is obliquely incident on a flow cell 1, and passes a position 1a of a communication portion 9. The laser beam then reaches a small phase mirror 40. The phase mirror 40 has a function of reflecting incident linearly polarized light to have a different direction of polarization. More specifically, light reflected by the phase mirror 40 and passing a position 1b has a different direction of polarization from that of light radiated on the position 1a. Light passing the position 1b is shielded by a light-shielding portion 41 arranged on a surface of the flow cell 1. Note that the phase mirror 40 also serves as a light stopper.

Members 23a, 33a, 43a, 23b, 33b, and 43b are polarization filters having characteristics for allowing only light components polarized in specific directions to selectively pass therethrough. A set of the polarization filters 23a, 33a, and 43a, and a set of the polarization filters 23b, 33b, and 43b are arranged so that their directions of polarization are perpendicular to each other. The polarization filters 23a, 33a, and 43a allow only polarized light components in the same direction as a laser beam from the laser light source 2 to pass therethrough, and shield polarized light components in other directions. The polarization filters 23b, 33b, and 43b allow only polarized light components in the same direction as a laser beam from the laser light source 3 to pass therethrough. As in the above embodiments, gains, i.e., detection sensitivities of outputs of light detectors 25, 35, and 45 are time-serially switched in synchronism with passage of specimens depending on kinds of light components to be detected.

The principle of measurement according to the present invention will be described below.

In general, most of scattered light components and fluorescence light components (90% or more) generated when a linearly polarized laser beam is radiated on a specimen have the same polarization characteristics as those of a radiated laser beam, and a few light components are converted into polarization-canceled light components. By utilizing this nature, the arrangement directions of the filters are set, so that the polarization filters 23a, 33a, and 43a allow only light components from the position 1a where a laser beam from the laser light source 2 is radiated to pass therethrough, and the polarization filters 23b, 33b, and 43b selectively allow only light components from the position 1b where a radiated laser beam has a different direction of polarization from that of the laser beam radiated on the position 1a to pass therethrough.

When a given specimen passes the examination region 1a, since an optical path of the polarization filter 23a is selected, of scattered light components and fluorescence light components generated by the specimen in the examination region 1a, only a light component which is reflected by the dichroic mirror 21a, and has a specific wavelength (the wavelength of the band-pass filter 22a) via the band-pass filter can selectively reach the light detector 25, and is detected by it. Similarly, scattered light components and fluorescence light components transmitting through the dichroic mirrors 21a and 21b are color-separated by the dichroic mirrors 31a and 31b having different wavelength characteristics, and reflected light components can reach the polarization filters 33a and 33b. In this case, only a light component reaching the polarization filter 33a is selected. Thus, only a light component which transmits through the dichroic mirror 21a, is reflected by the dichroic mirror 31a, and has a specific wavelength (the wavelength of the band-pass filter 32a) via the band-pass filter 32a is detected. Furthermore, light components transmitting through the dichroic mirrors 31a and 31b are reflected by the mirrors 41a and 41b, and reach the polarization filters 43a and 43b via the band-pass filters 42a and 42b having different wavelength characteristics. In this case, only a light component reaching the polarization filter 43a is selected. Thus, the light detector 45 detects only a light component having a specific wavelength (the wavelength of the band-pass filter 42a), which transmits through the dichroic mirrors 21a and 31a and the band-pass filter 42a.

When the specimen passing the examination region 1a reaches the examination region 1b after the lapse of a predetermined period of time, sideward scattered light components and fluorescence light components generated by the specimen from the position 1b have a different direction of polarization from that of light from the position 1a. Since these light components in this direction of polarization are selectively guided to the light detectors by the polarization filters 23b, 33b, and 43b having a different direction of polarization from that of the polarization filters 23a, 33a, and 43a, optical paths different from those described above are selected, and light components of specific wavelengths selected by the band-pass filters 22b, 32b, and 42b arranged in the selected optical paths are detected by the corresponding detectors.

As described above, the two-divided polarization filters arranged in front of the light detectors are selected to have different directions of polarization, and are arranged in correspondence with directions of polarization of the first and second laser beams, respectively. In other words, an optical path extending from the examination region to the light detector is divided into two paths, and the optical paths are switched in synchronism with passage of specimens. Thus, a light signal having a first direction of polarization and a light signal having a second direction of polarization can be time-serially distinguished from each other and can be sampled. As a result, by using the same light detectors and analogue processing system, two kinds of light signal can be measured per detector. Since detection levels are switched depending on kinds of light components to be detected as in the above embodiments, wide-range measurement can be achieved.

Note that the above embodiment employs the polarization filters. In place of the polarization filters, polarization members having the property of only allowing light components polarized in specific directions to pass therethrough may be adopted. For example, liquid crystal shutters may be used. In general, a liquid crystal shutter has a structure prepared by adhering two liquid crystal plates to each other. When a shutter is closed, it shields light components in all the directions of polarization. However, when the shutter is open, it serves as a kind of polarization filter, and transmits only a light component polarized in a specific direction therethrough but shields light components in other directions of polarization. Therefore, liquid crystal shutters are used in place of the polarization filter, and two liquid crystal shutters are orthogonally arranged in front of each detector, so that directions of polarization of the open shutters correspond to directions of polarization of radiation light beams. Thus, when the shutters are set in an open state, the same effects as those of the polarization filters can be obtained.

As another developed aspect, it is preferable that two liquid crystal shutters in front of each detector are subjected to opening/closing control in synchronism with passage of a specimen, so that a liquid crystal shutter for allowing light to pass therethrough is set in an open state, and a liquid crystal shutter for shielding light is set in a closed state. More specifically, when a specimen is located at the position 1a, the liquid crystal shutters at positions 23a, 33a, and 43a are set in an open state, and the liquid crystal shutters located at positions 23b, 33b, and 43b are set in a closed state. When a specimen is located at the position 1b, the open/closed states of these liquid crystal shutters are reversed. In this manner, a light-shielding effect of the closed shutters can be enhanced, and an S/N ratio can be further increased.

Fourth Embodiment

The fourth embodiment of the present invention will be described below. In recent years, demand has arisen for detection of other parameters such as light components in specific directions of polarization, polarization-canceled light components, and the like under the conditions including polarization in order to perform still detailed, precise analysis. This embodiment can meet this demand, and provides an apparatus which can obtain measurement parameters having polarization information in excess of the number of light detectors.

Figure 9:
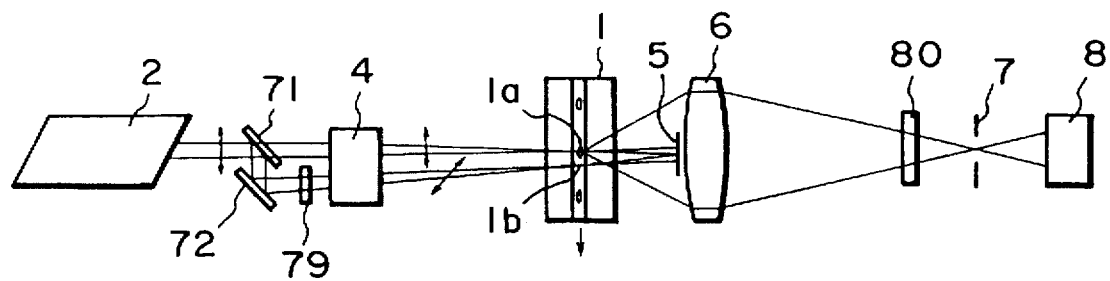
FIGS. 9 and 10 are diagrams showing the fourth embodiment of the present invention.
Figure 10:
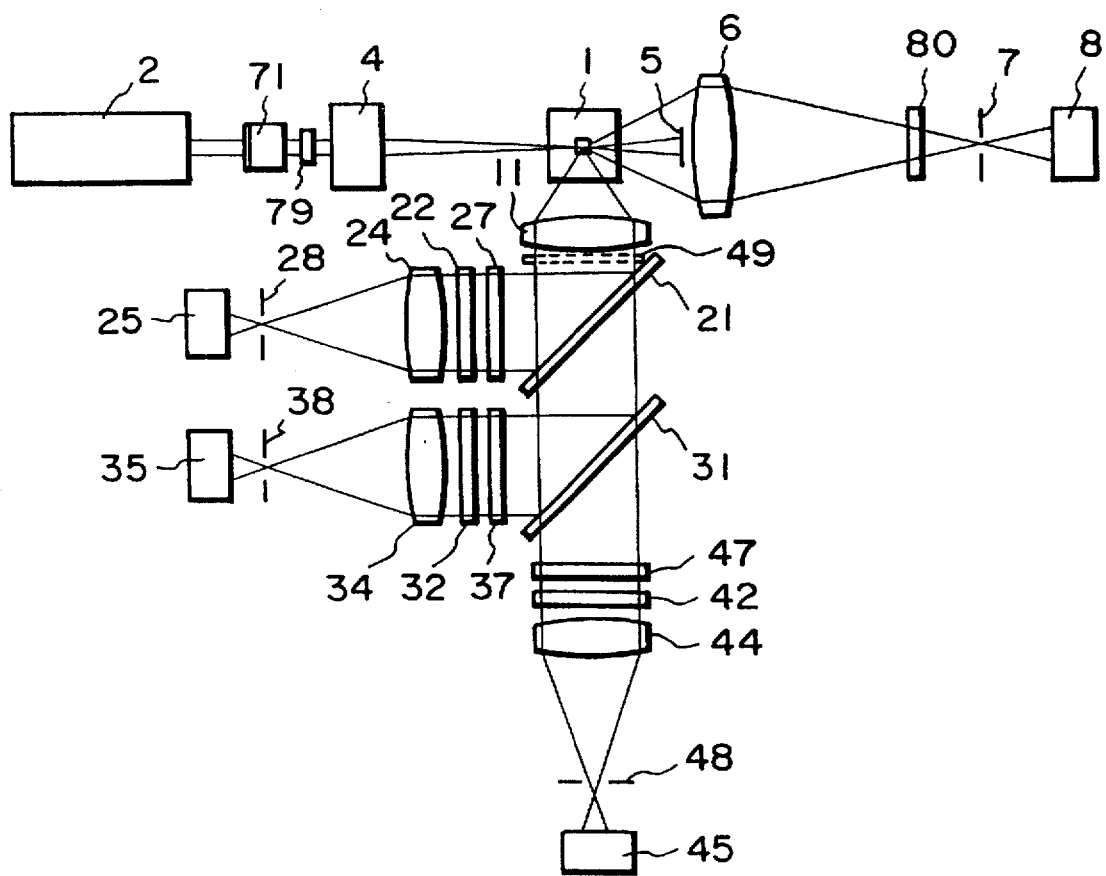

FIGS. 9 and 10 are diagrams of this embodiment. A laser light source 2 comprises an $Ar^+$ laser having a wavelength of 488 nm. The laser light source 2 is a linearly polarized laser beam source, and a generated laser beam is a beam linearly polarized in a predetermined direction. A laser beam emerging from the laser light source 2 is split into two beams by an optical system including a half mirror 71 and a return mirror 72. A $\lambda/2$ plate 79 is arranged in one optical path to change a direction of polarization of a light beam through 90°, so that directions of polarization of the two laser beams are perpendicular to each other. In this embodiment, the half mirror 71 has an unequal light amount division ratio, and a lower light beam has a higher intensity. However, the half mirror 71 may have an equal split ratio. Note that two laser light sources may be prepared, and may be orthogonally arranged to obtain two laser beams having orthogonal directions of polarization. In this case, the two laser beams may have different wavelengths. Alternatively, a simple optical system having the same effect as described above, as shown in FIG. 12, may be adopted.

A light stopper 5, a focusing lens 6 for focusing forward scattered light, a linearly polarized light filter 80 for selectively allowing a light component having the same direction of polarization as that of a laser beam radiated on a position 1a to pass therethrough, a field stop 7, and a light detector 8 for detecting forward scattered light are sequentially arranged in a beam straight propagation direction from the laser light source toward a flow cell, thus forming an optical system for detecting forward scattered light. Note that the field stop 7 has an aperture large enough to allow light components from both positions 1a and 1b to pass therethrough, and prevents noise light components from positions other than the positions 1a and 1b from being incident on the light detector 8. An output signal from the light detector 8 is also used as a trigger signal for determining sample timings of light detectors.

In a direction perpendicular to the laser beam straight propagation direction, a condenser lens 11 for condensing sideward scattered light and fluorescence light, and dichroic mirrors 21 and 31 for color-separating sideward scattered light and fluorescence light generated by a specimen are sequentially arranged. In a reflection direction of the dichroic mirror 21, a linearly polarized light filter 27, a band-pass filter 22 for selecting a wavelength of about 488 nm, a focusing lens 24, a field stop 28, and a light detector 25 are arranged, thus forming an optical system for detecting sideward scattered light. In a reflection direction of the dichroic mirror for separating green and red fluorescence light components, a linearly polarized light filter 37, a band-pass filter 32 for selecting a wavelength near that of green fluorescence light, a focusing lens 34, a field stop 38, and a light detector 35 are arranged, thus forming an optical system for detecting green fluorescence light. On the other hand, in a transmission direction of the dichroic mirror 31, a linearly polarized light filter 47, a band-pass filter 42 for selecting a wavelength near that of red fluorescence light, a focusing lens 44, a field stop 48, and a light detector 45 are arranged, thus forming an optical system for detecting red fluorescence light. Each linearly polarized light filter is arranged in a direction to selectively allow polarized light in the same direction of polarization as that of a laser beam radiated on the position 1a to pass therethrough. Note that as the light detectors 25, 35, and 45, photomultipliers having high detection sensitivity are suitable. As in the above embodiments, the gains, i.e., detection sensitivities of these light detectors 25, 35, and 45, and the light detector 8 can be time-serially switched in synchronism with passage of specimens.

A measurement operation in the apparatus with the above-mentioned arrangement will be described below.

In general, most of scattered light components and fluorescence light components (90% or more) generated when a linearly polarized laser beam is radiated on a specimen have the same polarization characteristics as those of a radiated laser beam, and a few light components are converted into polarization-canceled light components, as has been described in the above embodiment. Since polarized light and polarization-canceled light represent different pieces of information of a specimen, their light components can be used as effective information for specimen analysis.

In the flow cell, specimens sequentially flow. When a given specimen passes the examination region 1a wherein a laser beam in a specific direction of polarization, light scattering is caused by the specimen, and in this case, if the specimen is dyed with a fluorescence dyestuff, fluorescence light is also excited and generated together with scattered light.

The linearly polarized light filters 80, 27, 37, and 47 arranged in front of the light detectors are arranged in a direction for transmitting only light components having the same direction of polarization as that of a laser beam radiated on the position 1a, and shielding polarized light components in other directions, i.e., polarization-canceled light components. Thus, of the generated scattered light components, only a light component having the same direction of polarization as that of a radiated laser beam of forward scattered light is intensity-detected by the light detector 8, thus obtaining a forward scattered light signal. Of sideward scattered light components, a light component having the same direction of polarization as that of a radiated laser beam is intensity-detected by the light detector 25. Meanwhile, of fluorescence light components generated from the position 1a, a green fluorescence light component having the same direction of polarization as that of a radiated laser beam is intensity-detected by the light detector 35, and a red fluorescence light component having the same direction of polarization as that of a radiated laser beam is intensity-detected by the light detector 45. These measurement values have substantially the same meanings as parameters measured by the conventional apparatus.

When the specimen passing the examination region 1a reaches the examination region 1b after the lapse of a predetermined period of time, since a laser beam radiated on the position 1b has a direction of polarization perpendicular to that of the laser beam radiated on the position 1a, most of the scattered light components and fluorescence light components generated by the specimen from the position 1b have a direction of polarization perpendicular to that of light from the position 1a. Since the linearly polarized light filters 80, 27, 37, and 47 are arranged to selectively allow light components in the same direction of polarization as that of light from the position 1a to pass therethrough, most of scattered light components and fluorescence light components from the position 1b are shielded by these linearly polarized light filters. In this case, a few light components transmitting through the filters and reaching the light detectors are some of polarization-canceled light components. More specifically, intensities of scattered light components and fluorescence light components at the position 1b detected by the light detectors have information as polarization-canceled light components. In this embodiment, the half mirror 71 has an unequal split ratio, so that an intensity of a laser beam radiated on the position 1a is set to be larger than that at the position 1b. Furthermore, upon detection of polarized light and polarization-canceled light, detection levels of the light detectors are switched, so that very weak polarization-canceled light can be detected with a higher gain. Thus, very weak polarization-canceled light can be effectively detected. The polarization-canceled light serves as information effectively used for analyzing an internal structure of each specimen.

As described above, light intensities of forward scattered light, sideward scattered light, green fluorescence light, and red fluorescence light in a predetermined direction of polarization can be obtained at the position 1a, and polarization-canceled light components of these light components can be obtained at the position 1b. More specifically, a total of eight different measurement parameters can be obtained by the four light detectors.

In order to further simplify the arrangement of the above-mentioned apparatus, the linearly polarized light filters 27, 37, and 47 shown in FIG. 10 are omitted, and a linearly polarized light filter 49 may be arranged instead at a position indicated by a dotted line, thus obtaining the same effect as described above.

In this embodiment, the polarization filters are not employed. In place of the polarization filters, polarized light selection members having the property of selecting only a light component polarized in a specific direction, e.g., liquid crystal plates, polarization mirrors, polarization beams, and the like may be employed.

Fifth Embodiment

Figure 14:
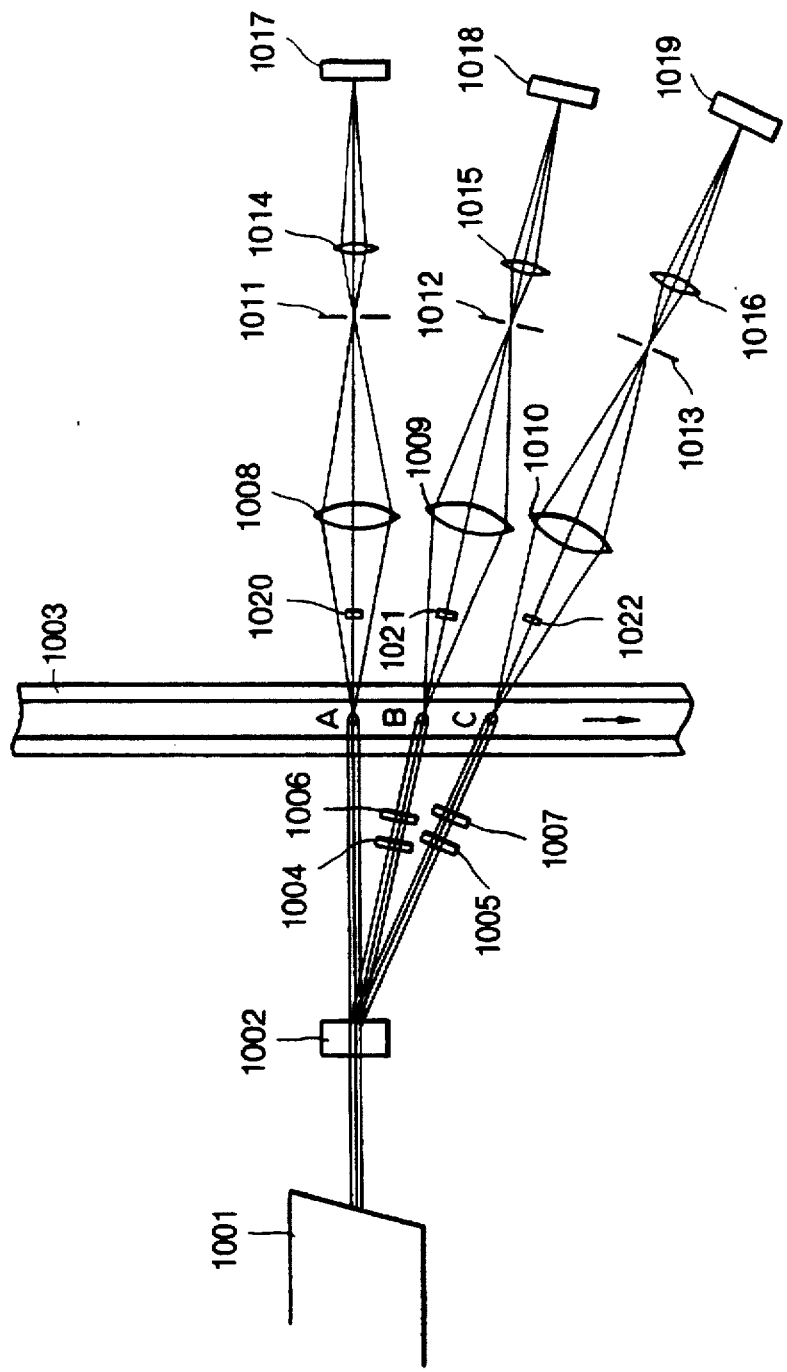
FIG. 14 is a diagram showing an arrangement of an optical system for detecting light scattered in forward or front directions according to a fifth embodiment of the present invention.
Figure 15:
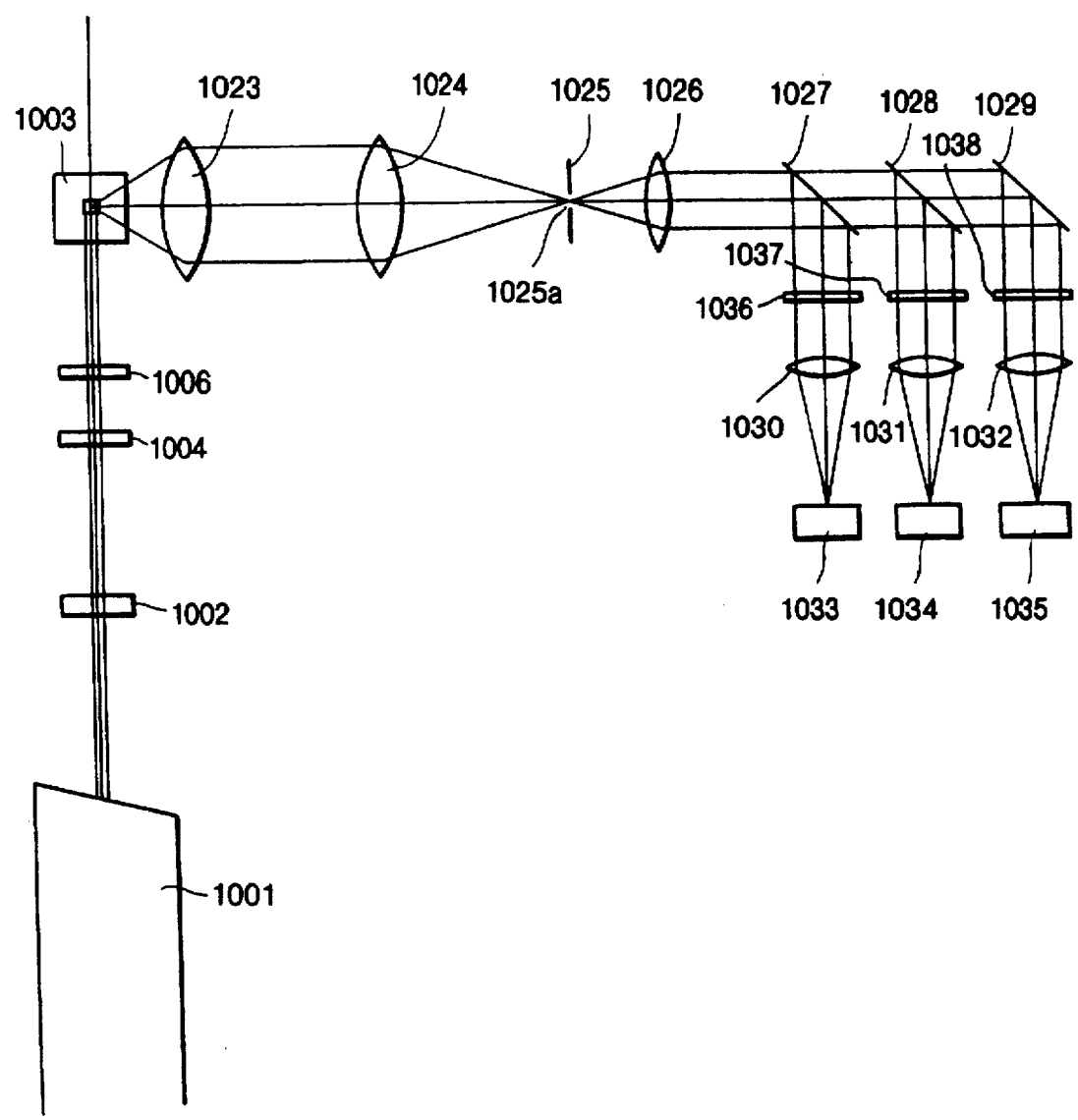
FIG. 15 is a diagram showing arrangement of an optical system for detecting light scattered in right angle or side directions and fluorescence in the FIG. 14 embodiment.

FIGS. 14 and 15 show the configuration of a fifth embodiment of the present invention. FIG. 14 is a diagram of the arrangement of an optical system for detecting light scattered in forward (front) directions in the apparatus of the present embodiment. FIG. 15 is a diagram in which the configuration shown in FIG. 14 is viewed from above, and shows the arrangement of an optical system for detecting light scattered in right angle (side) directions and fluorescence.

In FIG. 14, a laser light source 1001 emits laser light for measurement. An acousto-optical deflecting (AOD) device 1002 disposed in the optical path of the laser light has the function of changing the optical path of the laser light by changing the degree of deflection of the beam for the laser light source in accordance with a control signal from a control circuit (not shown). Within a flow cell 1003, there is provided a flow unit in which flow particles, such as blood cells, latex particles or the like. Laser beams in respective optical paths deflected and switched by the acousto-optical deflecting device 1002 are projected upon positions A, B and C in the flow unit of the flow cell 1003. In the midsection of the optical path to the position B, there are disposed a secondary harmonic generating (SHG) element 1004, such as KDP (potassium dihydrogen phosphate) or the like, having a nonlinear optical effect and a wavelength selection filter 1006 which passes only light having a wavelength equal to ½ the wavelength of light converted by the SHG element 1004. In the midsection of the optical path for the position C, there are disposed a fluorescent plate 1005 and a wavelength selection filter 1007 which passes only light having the wavelength of fluorescence from the fluorescent plate 1005. Light beams having different wavelengths are thereby projected upon positions A, B and C for inspection. In each optical path, there is disposed a light attenuating filter (not shown) so that the intensities of the light beams projected upon the positions A, B and C for inspection are equal. Although, in the present embodiment, an SHG element and a fluorescent plate are used as an example of members for converting wavelengths, any other members which convert the wavelength of incident light, such as fluorescent dyes, a Raman cell and the like, may also be used.

Furthermore, as another method for projecting light beams having different wavelengths upon respective portions for inspection, a multi-oscillation laser light source which simultaneously emits light beams having different wavelengths may be used, and wavelengths to be projected upon respective portions for inspection may be selected by wavelength selection filters. In this case, since a wavelength conversion member, such as an SHG element or the like, is not needed, the configuration becomes simpler.

The light beams scattered in forward (front) directions from the positions A, B and C for inspection (forward scatter A, B and C) are condensed by condenser lenses 1008, 1009 and 1010, respectively, and are independently detected by photodetectors 1017, 1018 and 1019 via diaphragms 1011, 1012 and 1013 and lenses 1014, 1015 and 1016, respectively. The diaphragms 1011, 1012 and 1013 have the function of stopping fields of view in order to pass only light beams from the positions A, B and C for inspection, respectively. In respective optical paths, there are disposed optical stoppers 1020, 1021 and 1022 behind the flow cell 1003, for the purpose of interrupting direct light beams which have passed through the flow cell 1003 without hitting a particle and light beams which have been transmitted by a particle so that these light beams do not enter the photodetectors. If other photodetectors are provided so as to detect the intensity of light beams at the positions of the stoppers, it is also possible to detect these transmitted light beams.

An optical system for detecting light beams scattered in side directions (right angle scatter) and fluorescence by a particle from positions for inspection will now be explained with reference to FIG. 15. FIG. 15 is a diagram of the arrangement when FIG. 14 is viewed from above. Light beams scattered in side directions and fluorescence which is emitted from a particle flowing in the vertical direction of the paper surface in the flow unit of the flow cell 1003 are condensed by a condenser lens 1023, pass through a lens 1024 and a diaphragm 1025. An opening 1025a in the diaphragm 1025 has the shape of a slit which is extended in the vertical direction of the paper surface. The opening 1025a passes light beams from the positions A, B and C for inspection, and interrupts other light beams. Among light beams which have passed through the diaphragm 1025, red fluorescence, green fluorescence and light beams scattered in side directions are detected by photodetectors 1033, 1034 and 1035, respectively, by a well-known optical arrangement consisting of a lens 1026, dichroic mirrors 1027, 1028 and 1029, wavelength selection filters 1036, 1037 and 1038, and lenses 1030, 1031 and 1032.

Figure 16:
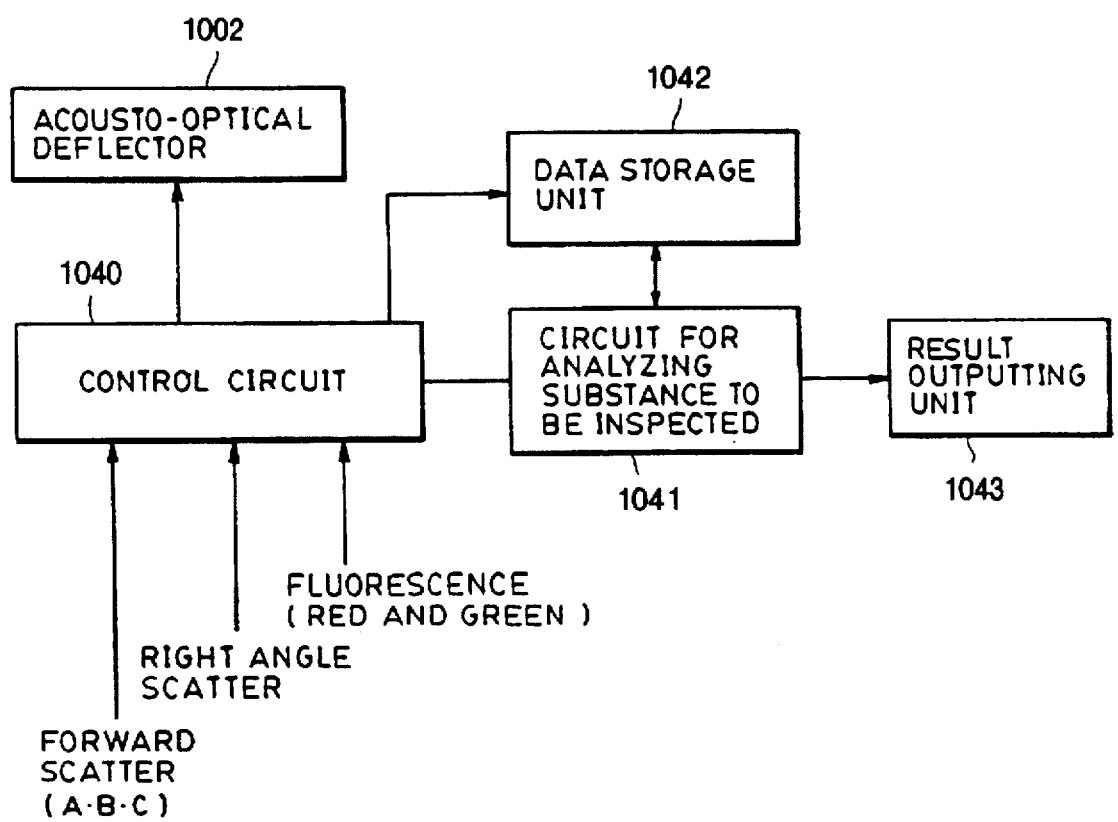
FIG. 16 is a block diagram showing the connection to an arithmetic processing unit.

Output pulses from the photodetectors 1017, 1018 and 1019 for detecting light beams scattered in front directions and output pulses from the photodetectors 1033, 1034, 1035 for detecting light beams scattered in side directions and fluorescence are output, for example, in the waveforms as shown in FIG. 17, and are input to a control circuit 1040 shown in FIG. 16. For the respective pulses thus input, the maximum pulse intensity, pulse widths, integrated values for the pulses and the like are measured, and are transmitted to and stored in a data storage unit 1042. According to the outputs of these pulses, the acousto-optical deflecting device 1002 is controlled to deflect irradiating beams in the direction of flow.

Next, a concrete method for control will be further explained in detail. By a sheath flow method which is well known in the field, a sample liquid is surrounded by a sheath liquid, and particles in the sample liquid sequentially flow one by one in the flow unit within the flow cell 1003. At the initial state, the beam of the irradiating laser light is fixedly projected upon the position A shown in FIG. 14. If a particle passes through the position A, scattered light or fluorescence is generated, and detected pulses of the scattered light as shown in FIG. 17 are obtained. At this time, it is arranged so that the light scattered in front directions from the point A is detected only by the photodetector 1017 due to the effect of the diaphragms 1011 through 1013. Light beams scattered in side directions and fluorescence are detected by the optical system shown in FIG. 15.

The control circuit 1040 monitors signals from the photodetector 1017, and determines that all the particles have passed through the position A when the generation of pulses due to the scattered light from the position A has ended. After this determination of passing, the frequency for control for the acousto-optical deflecting device 1002 is then changed to switch the position irradiated by the irradiating beam to the position B. The speed of control is sufficiently larger than the passing speed of the particle. That is, control is performed so that the position irradiated by the light beam is switched from the position A to the position B in a time which is sufficiently smaller than the time within which a particle moves from the position A to the position B, and the arrival of the particle is waited for at the position B. The wavelength of the light beam projected upon the position B is reduced by one half from the wavelength of the basic laser light from the laser light course 1001 by the SHG device 1004 and the wavelength selection filter 1006. Hence, it is possible to measure the same particle under a condition which is different from the condition at the position A. The light scattered in front directions emitted from the particle which has passed through the position B is detected only by the photodetector 1018, the light scattered in side directions and fluorescence are detected by the optical system shown in FIG. 15, and the detected data are stored.

After the measurement at the position B has been completed, the irradiating position is switched to the position C by the same control as described above. At the position C, the particle is measured by a light beam having a wavelength which is made different from those at the positions A and B by the fluorescent plate 1005 and the wavelength selection filter 1007. The detected data for the light scattered in front directions from the position C detected by the photodetector 1019, and the light scattered in side directions and fluorescence detected by the optical system shown in FIG. 15 are stored in the data storage unit 1042.

After the measurement at the position C has thus been completed and the measurement of one particle has been entirely completed, the irradiating position by the irradiating beam is returned to the initial position A, where the passing of the next particle is waited for, and the measurement operation is thereafter repeated in the same manner.

As the reference pulses for displacing the irradiating position by the laser, photometric pulses of light scattered in side directions, transmitted light or fluorescence may also or alternatively be used besides the pulses of light scattered in front directions as described above.

Since control is performed by the procedure described above, light is projected only upon a certain position at a certain moment. Accordingly, even if particles flow with very little time in between, a light beam can be projected only upon one particle in the course of measurement, and mismeasurement due to extrinsic light from other particles does not occur. Furthermore, the method of the present invention is not a method in which a light beam is projected upon a plurality of irradiating positions by dividing the light beam by a half mirror or a prism. Accordingly, energy loss is caused only due to the efficiency of an acousto-optical deflecting device (the efficiency is about 90%). It is therefore possible to efficiently utilize the power of a laser light source, and to obtain a large intensity of irradiating light.

When the measurement of the substance to be inspected in a sample has been entirely completed, a calculation for analyzing the substance to be inspected, such as statistical processing and the like, is performed by a circuit 1041 for analyzing the substance according to the measured data stored in the data storage unit 1042 shown in FIG. 16. Since concrete methods for analysis have become widely known through various literature, a detailed explanation thereof will be omitted. The result of the calculation is output to a result outputting unit 1043 by various methods, such as monitor display, printing out and the like.

The present invention encompasses various kinds of examples which are modified from the above-described embodiment. Some of them will hereinafter be explained.

FIG. 20 is a diagram for explaining a modified example. In FIG. 20, like components as those in FIG. 14 are indicated by like numerals.

An irradiating light beam emitted from the laser light source 1001 is deflected by the acousto-optical deflecting device 1002 in accordance with passing of a particle as in the above-described embodiment, and the optical path is switched. The irradiating light beams in respective optical paths are projected upon respective positions A, B and C in the flow unit of the flow cell 1003. The light beams scattered at the respective positions A, B and C are incident, for example, upon openings in an aperture (stopper) 1060 as depicted in FIG. 21, and only light beams scattered in front directions having a predetermined angle component are passed. The scattered light beams which have passed through the aperture 1060 are condensed by condenser lenses 1061 and 1062, and are subjected to photometry in a single photodetector 1066. Wavelength selection filters 1063 through 1065 are inserted in respective optical paths for detection. The filter 1063 passes only light having the wavelength of basic laser light emitted from the laser light source 1001. The filters 1064 and 1065 have characteristics which are identical to those of the filters 1006 and 1007, respectively. In order to perform photometry for light beams scattered in side directions and fluorescence, there is provided an optical system which is identical to that shown in FIG. 15.

According to the present embodiment, it is possible to reduce the number of condenser lenses and photodetectors for light beams scattered in front directions, which can lead to a reduction in cost.

In order to further reduce cost, the members 1004 and 1005 as wavelength conversion members and the wavelength selection filters 1006 and 1007 are removed, and a wavelength selection filter which passes light having the wavelength of red fluorescence and a wavelength selection filter which passes light having the wavelength of green fluorescence are used as the filters 1064 and 1065, respectively. That is, the apparatus has a configuration in which only scattered light is detected at the position A, only red fluorescence is detected at the position B, and only green fluorescence is detected at the position C. It thereby becomes possible to detect the scattered light and the red and green fluorescence using only the photodetector 1066, and it becomes unnecessary to provide the optical system for detecting light scattered in side directions shown in FIG. 15. The wavelengths of fluorescence to be detected are not limited to red and green. It is also advantageous to provide a member which converts the wavelength into a wavelength suitable for excitation of fluorescence without removing the wavelength conversion members 1004 and 1005.

FIG. 18 shows another modified example. In the first embodiment described above, the wavelength of irradiating light is changed and a plurality of measurements having different conditions are performed for each particle. On the other hand, the present embodiment is characterized in that the spot size and shape of irradiating light at a position for detection are changed.

Members 1050 through 1053 represent cylindrical lens units. The shapes of beam spots as shown, for example, in FIG. 19 are thereby obtained at positions A through D which are positions for inspection, respectively. The shapes at the positions A and B are for performing standard measurement, because light energy is widely dispersed and the tolerance for deviation in the flowing position of a particle is large. The shape at the position C is for performing measurement with high sensitivity because the energy density of light is high. The shape at the position D is for performing slit scan measurement for the particle of substance to be inspected. Sizes written in FIG. 19 are only examples. The most suitable sizes must be determined in accordance with the size of a particle, measuring conditions and the like. In the midsection of the optical path of the irradiating light for the position B, the SHG device 1004 and the wavelength selection filter 1006 are inserted as in the above-described embodiment. Hence, the shape of the beam spot and the wavelength of the irradiating light for the position B are different from those for other points.

Since the optical arrangement for detecting light beams scattered in front and side directions and fluorescence from respective positions, the configuration of a control/arithmetic circuit and the method for control are nearly identical to those in the first-described embodiment, a detailed explanation thereof will be omitted.

In the present embodiment, it is also possible to perform a plurality of measurements having different conditions for each particle, and to obtain a plurality of measurement parameters including various kinds of information.

Although in the embodiments described above there is the premise that irradiation having different irradiation conditions is performed at respective irradiating positions, irradiation may be performed under substantially identical conditions on respective irradiating positions as a further modified example. In this case, the apparatus may have a configuration in which members for changing conditions of irradiating light (wavelength conversion members or cylindrical lenses) are removed from the diagrams of the configurations for the above-described embodiments. For example, if the members 1004 and 1007 for converting the wavelength of light are removed from the configuration shown in FIG. 14, it becomes possible to irradiate light beams under identical conditions upon respective irradiating positions.

Thus, positions for inspection at a plurality of points are irradiated by light beams under identical conditions, each particle is measured a plurality of times under these identical conditions, and statistical values, such as an average value and the like, are calculated using a plurality of measured values for each particle thereby obtained to provide data for analysis. It thereby becomes possible to perform a measurement which has higher reliability than in conventional cases.

The fifth embodiment and various modified examples thereof have now been explained. However, the present invention is not limited to those aspects described above. Instead of changing only the wavelength or beam spot of irradiating light, the wavelength, and the size and shape of the beam spot of irradiating light may be simultaneously combined in various aspects, and each particle of the substance to be measured may be measured under two or more measurement conditions. It is thereby possible to greatly increase the amount of measured information compared with conventional cases.

Furthermore, conditions of being changed are not limited to the wavelength and beam spot of light, but polarization conditions, such as the degree of polarization, the direction of polarization and the like, of irradiating light or other conditions, such as the intensity of irradiating light and the like, may also be changed. In these cases, a light polarizing member or a light attenuating member, such as a $\lambda/2$ plate, a $\lambda/4$ plate, a polarizing filter, an attenuating filter or the like, may be disposed in each optical path.

According to the embodiments described above, it is possible to obtain a result of measurement under a plurality of conditions in one inspection operation for each particle of the substance to be inspected. Furthermore, contrary to the case of a conventional apparatus, light is projected upon only one point at one moment, and so mismeasurement due to extrinsic light from particles of the substance to be measured other than the one particle being measured does not occur. In addition, since only one light source is needed, the present invention has the effect of providing an apparatus with a compact size, low cost and low electric power consumption.

Figure 22:
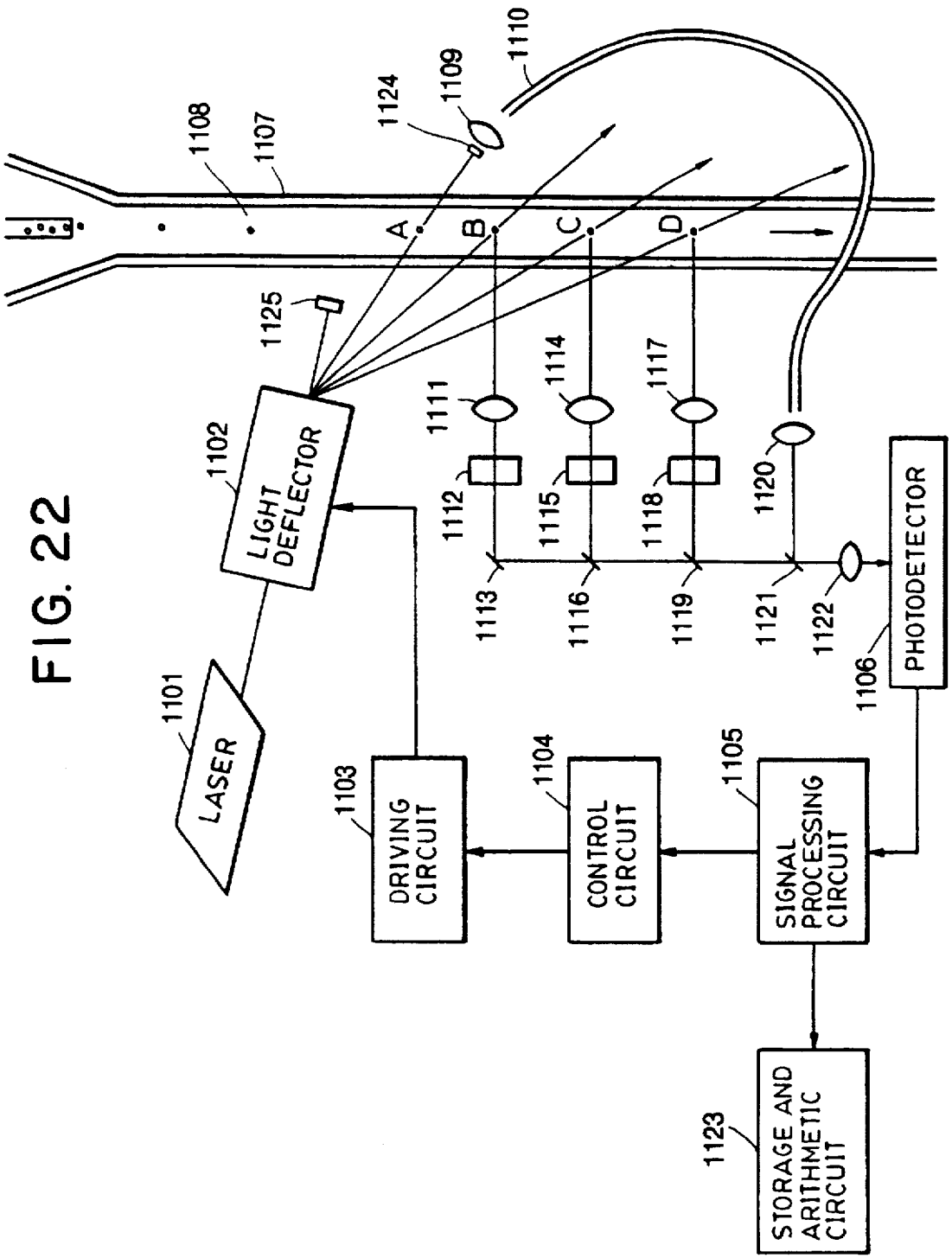
FIG. 22 is a diagram showing the configuration of a sixth embodiment of the present invention.

A sixth embodiment of the present invention will now be explained. FIG. 22 is a diagram of the configuration of the second embodiment of the present invention. Laser light from a laser light source 1101 as light irradiating means for irradiating a particle is incident upon a light deflector 1102 provided in the optical path. An acousto-optical deflecting (AOD) device is suitable for the light deflector 1102. The acousto-optical deflecting device can change the degree of deflection of incident light in accordance with frequency for control. The laser light deflected at the light deflector 1102 is projected upon a flow unit 1108 within a flow cell 1107. The 0-order light emitted from the light deflector 1102 is cut by a stopper 1125. A driving circuit 1103 generates a control frequency for controlling the degree of deflection by the light deflector 1102 to change the degree of deflection of the laser light. In the present embodiment, by changing the frequency in four staged predetermined values, it is possible to irradiate the laser light upon four positions along the direction of flow in the flow unit 1108.

Minute particles of the substance to be inspected, such as blood cells, latex particles and the like, in a sample are separated one by one or into blocks by the well-known sheath flow method, and the separated particles or blocks sequentially flow in the flow unit 1108 within the flow cell 1107 at a constant passing speed. The direction of flow of particles is from top to bottom in FIG. 22.

Each particle which successively flows past positions A, B, C and D shown in FIG. 22 is irradiated by the light at these positions, and photometry is performed for light scattered in front directions, light scattered in side directions, red fluorescence and green fluorescence, respectively. A stopper 1124 and a lens 1109 are disposed behind the position A on the optical axis, and an end portion of an optical fiber 1110 is disposed at a position which is conjugate with the position A relative to the lens 1109. In a side direction of the position B, there are disposed a lens 1111, a filter 1112 which selectively transmits the wavelength of the irradiating laser light, and a mirror 1113 in order. In a side direction of the position C, there are disposed a lens 1114, a filter 1115 which selectively transmits the wavelength of the red fluorescence, and a half mirror 1116. Similarly, in a side direction of the position D, there are disposed a lens 1117, a filter 1118 which transmits the wavelength of the green fluorescence, and a half mirror 1119.

Next, an explanation will be provided of a control method in which measurement is performed by deflecting the laser light and sequentially switching the irradiating position in synchronization with passing of a particle.

First, the laser light is fixedly projected upon a position A in FIG. 22 by controlling the light deflector 1102. When a particle arrives at the position A, scattered light and fluorescence are produced. Light beams scattered in front directions are measured at the position A. Among light beams produced at the position A, light beams scattered in front directions condensed by the lens 1109 enter an end of the optical fiber 1110. The stopper 1124 is provided on the optical axis to prevent the strong laser light from directly entering the optical fiber. Intensity of the light which has entered the one end of the optical fiber 1110 and come out from another end is detected by a photodetector 1106 via a lens 1120, a half mirror 1121 and a lens 1122.

When the intensity of the output pulse from the photodetector 1106 becomes 0 or not more than a predetermined threshold value, a signal processing circuit 1105 determines that the particle has passed through the point A, and transmits a signal to a control circuit 1104. The driving circuit 1103 then drives the light deflector 1102 so that the irradiating position by the laser light becomes the position B. By instantaneously switching the control frequency of the light deflector 1102, the irradiating position is also instantaneously switched, and it is possible to irradiate the laser light upon the point B before passage of the particle.

At the position B, light beams scattered in side directions are measured. Among scattered light beams emitted from the position B, light beams scattered in side directions relative to the optical axis of the laser light enter the lens 1111, only the wavelength of the laser light is selected by the filter 1112, and the intensity of the selected light beams is detected by the photodetector 1106 via the mirror 1113 and the lens 1122.

As in the case described before, when the intensity of the output pulse from the photodetector 1106 becomes 0 or not more than a predetermined threshold value, the signal processing circuit 1105 switches the irradiating position by the laser light from the position B to the position C.

Measurements at the points C and D are then performed in the same manner as described above. Measurements for red fluorescence and green fluorescence are performed at the positions C and D, respectively. When the measurement at the position D has been terminated, the irradiating position by the laser light is returned and fixed to the position A, where passage of the next particle is waited for.

Measurements are repeated in the same manner for many particles which successively pass through the flow unit, and measured data obtained are subjected to statistical processing and the like at a storage and arithmetic circuit 1123, and analysis is performed. Relative to concrete methods of analysis, various methods have been developed and become known in the related field, and hence an explanation thereof will be omitted.

The present invention is not limited to the embodiments described above. Detection for all light beams is not necessarily performed by a single photodetector, but it suffices if a photodetector detects plural kinds of light beams. In general, the intensity of light scattered in front directions is large, and the intensity of other light beams, particularly of fluorescence, is weak. Hence, for measuring both light scattered in front directions and fluorescence in a single photodetector, it is necessary to provide a photodetector which has a wide dynamic range. Accordingly, if it is arranged, for example, so that a single photodetector having high sensitivity is used for the detection of red and green fluorescence, another photodetector is used for the detection of light beams scattered in front directions and side directions, and measurement is sequentially performed with time-shifting, it is possible to use photodetectors which are generally used, such as photomultipliers or the like. In this case, since it is possible to simultaneously detect light scattered in front directions and fluorescence at an identical point, the number of measurements per particle is decreased. Hence, this approach also has the effect of shortening the total time for measurements.

In conventional apparatuses, a plurality of photodetectors each dedicated for the kind of light to be detected have been needed. According to the present embodiments, however, plural kinds of optical signals are detected by a single photodetector while being switched. That is, in conventional apparatuses, a plurality of dedicated photodetectors have been provided for respective parameters, such as green fluorescence, red fluorescence, scattered light and the like, and a plurality of parameters have simultaneously been measured. To the contrary, the present embodiments are characterized in that each parameter is time-serially and nonsimultaneously measured by a photodetector with time-shifting. As a result, a smaller number of photodetectors is needed, and it also becomes possible to provide a compact and low-cost apparatus. Furthermore, since a photodetector is used in common, no error due to variations in sensitivity is produced.

Moreover, contrary to in the case of a conventional apparatus, since light is projected upon only one point at a moment, mismeasurement due to extrinsic light from particles other than a particle being measured does not occur. In addition, since only one light source is needed, the present invention has the effects to provide an apparatus with a compact size, low cost and low electric power consumption.

What is claimed is:

1. A specimen measurement apparatus comprising:

a flow path through which specimens individually pass;

irradiation means for irradiating first and second radiation beams on first and second positions along the flow path spaced apart from each other in a moving direction of the specimens;

a light detector for time-serially detecting light components emerging from specimens passing the first and second positions;

a first aperture arranged at a position conjugate with the first position to define a first optical path extending from the first position to said light detector;

a second aperture arranged at a position conjugate with the second position to define a second optical path extending from the second position to said light detector, which is different from the first optical path;

a first optical filtering member arranged in said first optical path for filtering the light component having the first optical characteristic; and a second optical filtering member, arranged in said second optical path for filtering the light component having the second optical characteristic, wherein the light detector is arranged at a position conjugate with the first and second apertures.

2. An apparatus according to claim 1, wherein said irradiation means comprises a first light source for generating the first radiation beam, and a second light source for generating the second radiation beam.

3. An apparatus according to claim 1, wherein said irradiation means comprises means for splitting a radiation beam from one light source into two light beams to generated the first and second radiation beams.

4. An apparatus according to claim 1, wherein said irradiation means comprises a laser light source.

5. An apparatus according to claim 1, wherein the first and second radiation beams have different wavelengths.

6. An apparatus according to claim 1, wherein the optical characteristic is a wavelength of light.

7. An apparatus according to claim 1, wherein the specimen has a cell.

8. An apparatus according to claim 1, wherein the specimen has a carrier particle.

9. An apparatus according to claim 1, further comprising storage means for storing a value detected by said light detector as measurement data.

10. An apparatus according to claim 9, further comprising analysis means for analyzing the specimens on the basis of the data stored in said storage means.

11. An apparatus according to claim 10, further comprising output means for outputting an analysis result of said analysis means.

12. An apparatus according to claim 1, further comprising means for forming a sheath flow to sequentially allow individual specimens to pass therethrough.

13. An apparatus according to claim 1 further comprising
determination means for determining that a plurality of specimens pass first and second positions at substantially the same time; and
means for cancelling detection by said light detection means on the basis of a determination result of said determination means.

14. An apparatus according to claim 13, wherein said determination means comprises:
means for independently detecting a timing at which the specimen passes the first position, and a timing at which the specimen passes the second position, and comparing the two timings.

15. An apparatus according to claim 13, wherein said determination means comprises:
means for detecting a timing at which the specimen passes the first position; and
means for detecting whether or not another specimen passes the first position with a predetermined period from the detected timing.

16. An apparatus according to claim 1, further comprising:
setting means for setting a measurement mode;
first radiation means for generating a first radiation beam, and radiating the beam at a first position where the specimen passes;
second radiation means for generating a second radiation beam, and radiating the beam at a second position different form the first position;
light detection means for time-serially detecting light components having first and second optical characteristics different from each other and emerging from the specimens passing the first and second positions using the same light; and
control means for controlling a presence/absence of operations of said first and second radiation means in accordance with the set measurement mode.

17. An apparatus according to claim 16, wherein said control means switches between a mode for operating one of said first and second radiation means, and inactivating the other radiation means, and a mode for operating both said first and second radiation means in accordance with the measurement mode set by said setting means.

18. An apparatus according to claim 17, wherein said first and second radiation means comprise laser light sources, and when the radiation means is inactivated, said laser light source is set in a sleep mode or a power source of said light source is cut off.

19. A specimen measurement method comprising:

a step of time-serially irradiating first and second radiation beams onto individual specimens;

a first detection step of selecting a light component having a first optical characteristic of light components emerging from a specimen when the first radiation beam is irradiated, and causing a light detector to detect the selected light component;

a second detection step of selecting a light component having a second optical characteristic of light components emerging from the specimen when the second radiation beam is irradiated, and causing the same light detector to detect the selected light component; and a step of changing a detection sensitivity of said light detector in synchronization with the irradiation of the first and second radiation beams.

20. A method according to claim 19, further comprising:

the step of determining that a plurality of specimens pass the first and second positions at substantially the same time; and the step of cancelling detection by said light detector on the basis of a determination result.

21. A method according to claim 19, further comprising the step of performing a pre-treatment of specimens in advance.

22. A method according to claim 19, further comprising the step of analyzing the specimen on the basis of a value detected by said light detector.

23. A method according to claim 19, wherein the radiation beam is a laser beam.

24. An apparatus for inspecting particles comprising:

a flow path through which the particles individually pass;

a light source for generating a light beam;

a deflector for deflecting said light beam along a direction of said flow path;

a controller for controlling the deflector to switch a deflection angle of said light beam, stepwise in synchronization with passing of the particle; and a detector for detecting light from the particle which is irradiated with said light beam.

25. An apparatus according to claim 24, wherein the controller controls the deflector so as to switch step-by-step a position where the light beam is irradiated.

26. An apparatus according to claim 25 wherein said position is switched in advance of passing of the articles.

27. An apparatus according to claim 24, wherein said deflector comprises an acousto-optical deflecting device.

28. An apparatus according to claim 24, wherein said detector detects scattered light and/or fluorescent light from said particle.

29. An apparatus according to claim 24, wherein said particles flow through a flow cell.

30. An apparatus according to claim 24, wherein said particles are cells.

* * * * *

UNITED STATES PATENT AND TRADEMARK OFFICE
CERTIFICATE OF CORRECTION

PATENT NO. : 5,760,900
DATED : June 2, 1998
INVENTOR(S) : YUJI ITO, ET AL.

Page 1 of 2

It is certified that error appears in the above-identified patent and that said Letters Patent is hereby corrected as shown below:

On the title page,

AT [56] REFERENCES CITED

OTHER PUBLICATIONS

"SteinKamp et al.," should read --Steinkamp et al.,--.

COLUMN 4

Line 1, "time" should read --time- --; and
Line 29, "FIGS. 11A to 12" should read --FIGS. 11A-11D and 12--.

COLUMN 7

Line 41, "radiation" should read --radiation at--; and
Line 48, "radiation" should read --radiation at--.

COLUMN 8

Line 43, "system," should read --system--.

COLUMN 9

Line 63, "and input" should read --are input--.

COLUMN 11

Line 7, "32a, and 33a" should read --33a, and 43a--.

UNITED STATES PATENT AND TRADEMARK OFFICE
CERTIFICATE OF CORRECTION

PATENT NO. : 5,760,900
DATED : June 2, 1998
INVENTOR(S) : YUJI ITO, ET AL.

It is certified that error appears in the above-identified patent and that said Letters Patent is hereby corrected as shown below:

COLUMN 14

Line 58, "have" should read --having--.

COLUMN 21

Line 66, "course 1001" should read --source 1001--.

COLUMN 27

Line 36, "member," should read --member--; and
Line 48, "ated" should read --ate--.

COLUMN 28

Line 4, "claim 1" should read --claim 1,-- and
"comprising" should read --comprising:--; and
Line 31, "form" should read --from--.

COLUMN 30

Line 8, "claim 25" should read --claim 25,--.

Signed and Sealed this

Third Day of August, 1999

Attest:

Q. TODD DICKINSON

*Attesting Officer*     *Acting Commissioner of Patents and Trademarks*